(12) United States Patent
Dalibey et al.

(10) Patent No.: US 11,773,257 B2
(45) Date of Patent: Oct. 3, 2023

(54) BIODEGRADABLE POLYESTER ARTICLE COMPRISING ENZYMES

(71) Applicant: CARBIOLICE, Riom (FR)

(72) Inventors: Mediha Dalibey, Clermont-Ferrand (FR); Clementine Arnault, Clermont-Ferrand (FR); Nadia Auclair, Cournon d'Auvergne (FR)

(73) Assignee: CARBIOLICE, Riom (FR)

( * ) Notice: Subject to any disclaimer, the term of this patent is extended or adjusted under 35 U.S.C. 154(b) by 782 days.

(21) Appl. No.: 16/642,196

(22) PCT Filed: Aug. 31, 2018

(86) PCT No.: PCT/EP2018/073416
§ 371 (c)(1),
(2) Date: Feb. 26, 2020

(87) PCT Pub. No.: WO2019/043134
PCT Pub. Date: Mar. 7, 2019

(65) Prior Publication Data
US 2020/0199354 A1    Jun. 25, 2020

(30) Foreign Application Priority Data
Aug. 31, 2017 (EP) .................... 17188781

(51) Int. Cl.
| | | |
|---|---|---|
| *C08L 67/04* | (2006.01) | |
| *C08J 3/22* | (2006.01) | |
| *C12N 9/54* | (2006.01) | |
| *B29C 48/08* | (2019.01) | |
| *B29C 48/10* | (2019.01) | |
| *B29C 48/00* | (2019.01) | |
| *B29K 67/00* | (2006.01) | |

(52) U.S. Cl.
CPC ............ *C08L 67/04* (2013.01); *C08J 3/226* (2013.01); *C12N 9/54* (2013.01); *C12Y 304/21014* (2013.01); *B29C 48/0018* (2019.02); *B29C 48/08* (2019.02); *B29C 48/10* (2019.02); *B29K 2067/046* (2013.01); *B29K 2995/006* (2013.01); *C08L 2201/06* (2013.01); *C08L 2205/025* (2013.01); *C08L 2310/00* (2013.01)

(58) Field of Classification Search
CPC ................. C08L 67/04; C08L 2201/06; C08L 2205/025; C08L 2310/00; C08J 3/226; C12N 9/54; C12Y 303/21014; B29C 48/08; B29C 48/10; B29C 48/0018; B29K 2067/046; B29K 2995/006
See application file for complete search history.

(56) References Cited

U.S. PATENT DOCUMENTS

| | | |
|---|---|---|
| 5,739,244 A | 4/1998 | Fisk |
| 6,176,915 B1 | 1/2001 | Franke et al. |
| 2004/0167247 A1 | 8/2004 | Han et al. |

FOREIGN PATENT DOCUMENTS

| | | |
|---|---|---|
| FR | 2856405 B1 | 2/2006 |
| FR | 2903042 B1 | 12/2010 |
| JP | 2002-362578 | 12/2002 |
| WO | WO2004113433 A1 | 12/2004 |
| WO | WO2010041063 A2 | 4/2010 |
| WO | WO2013093355 A1 | 6/2013 |
| WO | 2014079844 A1 | 5/2014 |
| WO | WO2016062695 A1 | 4/2016 |
| WO | WO2016146540 A1 | 9/2016 |
| WO | WO2016198650 A1 | 12/2016 |
| WO | WO2016198652 A1 | 12/2016 |

OTHER PUBLICATIONS

Wandrey et al. "Materials for Encapsulation", Encapsulation Technologies for Active Food Ingredients and Food Processing, 2010, pp. 31-100.

*Primary Examiner* — Edward J Cain
(74) *Attorney, Agent, or Firm* — BCF LLP

(57) ABSTRACT

Biodegradable polyester article comprising enzymes. The present invention relates to novel biodegradable plastic articles comprising a polyester and biological entities able to degrade such polyester, and wherein the biological entities are homogeneously dispersed in the plastic articles. The invention also relates to a process for producing such plastic articles, comprising a step of mixing biological entities with a selected carrier in a liquid composition or in a masterbatch with the polyester.

27 Claims, No Drawings

BIODEGRADABLE POLYESTER ARTICLE COMPRISING ENZYMES

FIELD OF THE INVENTION

The present invention relates to novel biodegradable plastic articles comprising a polyester and biological entities able to degrade such polyester, and wherein the biological entities are homogeneously dispersed in the plastic articles. The invention also relates to a process for producing such plastic articles, comprising a step of mixing biological entities with a selected carrier in a liquid composition or in a masterbatch with the polyester.

BACKGROUND OF THE INVENTION

Different biodegradable plastic compositions have been developed in order to answer to plastic environmental issues and the piling up of plastic articles in landfill sites and in natural habitats, and to comply with restrictive legislation in particular about short-lived products (such as bags, packaging including trays, containers, bottles, agricultural films, etc.).

These plastic compositions generally contain polyester, flours or starches coming from diverse cereals (U.S. Pat. Nos. 5,739,244; 6,176,915; US 2004/0167247; WO 2004/113433; FR 2 903 042; FR 2 856 405). Various solutions were proposed to improve the control of the degradation of these plastics by mineral chemical additives (WO 2010/041063) or by the inclusion of biological entities capable of degrading polyesters (WO 2013/093355; WO 2016/198652; WO 2016/198650; WO 2016/146540; WO 2016/062695). The resulting plastic article contains biological entities, particularly enzymes dispersed in a polymer, and has an improved biodegradability as compared to plastic articles deprived of such biological entities.

If the manufacture of articles comprising polyester and enzymes has already been described, its implementation may raise technical problems regards to the homogeneity, the surface roughness and the mechanical properties of the article obtained. The known or suggested methods of manufacture lead to inhomogeneous articles which exhibit aggregates of enzymes. An inhomogeneity in the distribution of the enzymes in the plastic composition has many disadvantages in terms of physical properties, and aesthetical point of view. In particular, it does not make possible to produce thin films. In some instance, the degrading activity of the biological entities may be affected by these methods of the art.

The present invention thus provides biodegradable plastic articles exhibiting a homogenous dispersion of the enzymes in the article leading to expected physical performances. The present invention also provides plastic articles with an improved degradability.

SUMMARY OF THE INVENTION

The invention provides new biodegradable plastic articles comprising at least one polyester and biological entities, and exhibiting expected physical and degradation performances.

It is thus an object of the invention to provide a biodegradable plastic article, comprising at least one polyester and biological entities having a polyester-degrading activity, wherein the biological entities are able to degrade said polyester and are homogeneously dispersed in the plastic article.

The invention provides a biodegradable plastic article comprising at least one polyester and biological entities having a polyester-degrading activity, wherein it comprises a carrier selected among polysaccharides and optionally a polymer having a melting temperature below 140° C. and/or a glass transition temperature below 70° C. (a carrier polymer) and mixtures thereof, the biological entities being able to degrade said polyester and being homogeneously dispersed in the plastic article.

Particularly the invention provides for a plastic article comprising, based on the total weigh of the plastic article:
from 10 to 98% of polylactic acid (PLA)
from 0 to 40% of a polysaccharide
from 0 to 40% of a carrier polymer, provided that when one of the polysaccharide or the polymer is 0% the other one is not null, and
from 0.01 to 10% of biological entities having a PLA-degrading activity homogeneously dispersed in the plastic article.

The invention also provides for a process for preparing a plastic article comprising at least one polyester and biological entities having a polyester-degrading activity homogeneously dispersed in the plastic article, said process, comprising a step (a) of mixing between 0.01% and 10% by weight of biological entities having a polyester-degrading activity with a least said one polyester and a step (b) of shaping said mixture of step (a) in a plastic article, wherein the biological entities are mixed during step (a) under a form appropriate for allowing homogeneous dispersion of the said biological entities in the plastic article, selected among
a liquid composition comprising the biological entities having a polyester-degrading activity, a carrier and water, or
a masterbatch comprising the biological entities having a polyester-degrading activity and a carrier polymer having a melting temperature below 140° C. and/or a glass transition temperature below 70° C.

The invention also provides for a method for increasing the homogeneity of dispersion of biological entities in a plastic article comprising a polyester, said method comprising introducing during the process of production of such plastic article, the biological entities under the form of a liquid composition comprising the biological entities having a polyester-degrading activity, a carrier and water, or under the form of a masterbatch comprising the biological entities having a polyester-degrading activity and a carrier polymer having a melting temperature below 140° C. and/or a glass transition temperature below 70° C.

The invention also provides for a masterbatch comprising biological entities having a polyester-degrading activity and a carrier polymer having a melting temperature below 140° C. and/or a glass transition temperature below 70° C. and optionally a polysaccharide.

DETAILED DESCRIPTION OF THE INVENTION

The present invention relates to novel plastic articles, with improved homogenous dispersion of the biological entities, particularly enzymes and methods for producing them. The invention shows that such articles, with suitable distribution rate of active biological entities, are of particular interest to answer the physical and degradation characteristics expected for single-use and short-lived plastic articles.

Definitions

The present disclosure will be best understood by reference to the following definitions.

Within the context of the invention, the term "plastic article" refers to any item made from at least one polymer, such as plastic sheet, film, tube, rod, profile, shape, massive block, fiber, etc. Preferably, the plastic article is a manufactured product, such as a rigid or flexible packaging, agricultural films, bags and sacks, disposable items or the like. Preferably, the plastic article comprises a mix of semi-crystalline and/or amorphous polymers, or semi-crystalline polymers and additives. The plastic articles may contain additional substances or additives, such as plasticizers, mineral or organic fillers. According to the invention, the plastic article may be selected from a plastic film or a rigid plastic article.

According to the invention, the term "plastic film" refers to a flexible sheet of plastic (i.e., capable of being flexed without breaking) with a thickness below 250 µm. Thin film are considered to have a thickness below 100 µm, preferably below 50 µm and are preferably produced by blown-film extrusion, whereas thick film have a thickness above 100 µm and are preferably produced by cast film extrusion. Examples of plastic films include agricultural films, plastic bags or sacks, films for flexible packaging, food films, mailing films, liner films, multipack films, industrial films, personal care films, nets, etc.

According to the invention, the term "rigid plastic article" refers to a plastic article which is not a film. These articles are preferably produced by calendering, injection-molding, thermoforming, blow molding, or even by rotomolding and 3D printing. Examples of rigid plastic articles are thin wall packaging such as food and beverage packaging, boxes, trays, containers, food service ware, electronics casings, cosmetic cases, outdoor gardening items such as pots, rigid packaging, containers, cards, cotton swabs, irrigation pipes, etc. Some rigid plastic articles may be produced by thermoforming plastic sheets with a thickness of 250 µm or more, such plastic sheets being produced by film casting or calendering.

According to the invention the rigid plastic article has a thickness below 5 mm, preferably below 3 mm.

As used herein, the terms "plastic composition" designates a mixture of polymers and biological entities, and eventually additional compounds (e.g., additives, filler, etc.) before any shaping step or conditioning step to produce a plastic article. In a particular embodiment of the invention the plastic composition is a masterbatch under a solid form, before its introduction in a polyester-based matrix.

A "polyester-based matrix" refers to a matrix comprising, as the main ingredient, one or more polyester(s). The polyester-based matrix comprises at least 51% by weight of polymer (s), based on the total weight of the composition, preferably at least 60% or 70%. The polyester-based matrix may further comprise additional compounds, such as additives. According to the invention, the polyester-based matrix is deprived of any biological entities.

As used herein, the term "masterbatch" designates a concentrated mixture of selected ingredients (e.g., biological entities, additives, etc.) and polymer that can be used for introducing said ingredients into plastic articles or compositions in order to impart desired properties thereto. Masterbatch compositions allow the processor to introduce selected ingredients economically during plastic manufacturing process. Advantageously, the masterbatch is composed of a polymer wherein the selected ingredients are incorporated in high concentration. Generally, the masterbatch is dedicated to be mixed with polyester(s) or a polyester-based matrix to produce a final plastic having a desired amount of selected ingredients. The masterbatch may further comprise mineral or organic fillers. According to the invention, the masterbatch comprises at least 5% of a composition of biological entities having a polyester-degrading activity. In the context of the invention, the polymer of the masterbatch is preferably selected from a polymer with a melting temperature (Tm) below 140° C. With regards to amorphous polymer, the Tm refers to the transformation temperature at which the amorphous polymer is fluid enough to be processed by extrusion (i.e., in a rubbery or softened state).

A "polymer" refers to a chemical compound or mixture of compounds whose structure is constituted of multiple repeating units linked by covalent chemical bonds. Within the context of the invention, the term "polymer" includes natural or synthetic polymers, comprising a single type of repeating unit (i.e., homopolymers) or different types of repeating units (i.e., block copolymers and random copolymers). As an example, synthetic polymers include polymers derived from petroleum oil or biobased polymers, such as polyolefins, aliphatic or aromatic polyesters, polyamides, polyurethanes and polyvinyl chloride. Natural polymers include lignin and polysaccharides, such as cellulose, hemicellulose, starch and derivatives thereof that may or may not be plasticized.

Within the context of the invention, the term "polyester" refers to a polymer that contains an ester functional group in their main chain. Ester functional group is characterized by a carbon bound to three other atoms: a single bond to a carbon, a double bond to an oxygen, and a single bond to an oxygen. The single bound oxygen is bound to another carbon.

According to the composition of their main chain, polyesters can be aliphatic, aromatic or semi-aromatic. Polyester can be homopolymer or copolymer. As an example, polylactic acid is an aliphatic homopolymer composed of one monomer, lactic acid; and polyethylene terephthalate is an aliphatic-aromatic copolymer composed of two monomers, terephthalic acid and ethylene glycol. Such polyesters may be native or chemically modified. In the context of the invention, the term "filler" refers to a substance that is incorporated to a plastic composition and/or to a plastic article to reduce the costs thereof or, optionally, improve the physical properties thereof (e.g., its hardness, stiffness or strength). Fillers can be inactive (i.e., inert) or active material, and may form chemical bonds with the components of the plastic composition or article. The filler can be natural, synthetic or modified fillers. The filler can be selected from mineral or organic fillers. In a particular embodiment of the invention, the mineral filler is chosen from the group consisting without limitation of calcite, carbonate salts or metal carbonate such as calcium carbonate (or limestone), potassium carbonate, magnesium carbonate, aluminium carbonate, zinc carbonate, copper carbonate, chalk, dolomite, silicate salts such as hydrous magnesium silicate such as talc or soapstone, calcium silicate (wollastonite), potassium silicate, magnesium silicates (talc), aluminium silicate (kaolin), or mix thereof such as mica, smectite such as montmorillonite, vermiculite, and palygorskite-sepiolite, sulphate salts such as barium sulfate, or calcium sulfate (gypsum), mica, hydroxide salt or metal hydroxide such as calcium hydroxide or potassium hydroxide (potash) or magnesium hydroxide or aluminium hydroxide or sodium hydroxide (caustic soda), hydrotalcite, metal oxide or oxide salts such as oxide of magnesium or oxide of calcium or oxide of aluminium or iron oxide or copper oxide, clay, asbestos, silica, graphite, carbon black, metal fibers or metal flakes, glass fibers, magnetic fillers, aramid fibers, ceramic fibers and derivatives thereof or blends/mixtures of these materials.

Alternatively or in addition, the organic filler is chosen from the group consisting of wood flour, plant or vegetable flour such as cereal flour (corn flour, wheat flour, rice flour, soy bean flour, nutshell flour, clam shell flour, corn cob flour, cork flour, rice hull flour); saw dust; plant fibers such as flax fibers, wood fibers, hemp fibers, bamboo fibers, chicken feathers and derivatives thereof or blends/mixtures of these materials. Natural polymers can also be used as organic fillers, such as lignin, or polysaccharides such as cellulose or hemi-cellulose, starch, chitin, chitosan and derivatives or blends/mixtures of these materials.

As used herein, the term "biological entities" designates active enzymes or enzyme-producing microorganisms, such as sporulating microorganisms, as well as combinations thereof. According to the invention, "biological entities" preferably refer to enzymes. The biological entities may be in solid (e.g., powder) or liquid form.

Within the context of the invention, the term "liquid composition" corresponds to a composition in a fluid form, i.e. which takes the form of the container it is included in. In the context of the invention, the composition is in a liquid form at room temperature and/or at the temperature of its incorporation in a partially or totally molten polymer. As used herein the term "polysaccharides" refers to molecules composed of long chains of monosaccharide units bound together by glycosidic linkages. Polysaccharides structure can be linear to highly branched. Examples include storage polysaccharides such as starch and glycogen, and structural polysaccharides such as cellulose and chitin. Polysaccharides include native polysaccharides or chemically modified polysaccharides by cross-linking, oxidation, acetylation, partial hydrolyze, etc. Carbohydrate polymers may be classified according to their source (marine, plant, microbial or animal), structure (linear, branched), and/or physical behavior (such as the designation as gum or hydrocolloid which refers to the property that these polysaccharides hydrate in hot or cold water to form viscous solutions or dispersions at low concentration gum or hydrocolloid). In the context of the invention, the polysaccharides may be classified according to the classification described in "Encapsulation Technologies for Active Food Ingredients and Food Processing—Chapter 3—Materials for Encapsulation—Christine Wandrey, Artur Bartkowiak, and Stephen E. Harding":

Starch and derivatives, such as amylose, amylopectine, maltodextrin, glucose syrups, dextrin, cyclodextrin.

Cellulose and derivatives, such as methylcellulose, hydroxypropyl methyl cellulose, ethyl cellulose, etc.

Plant exudates and extracts, also called plant gums or natural gums, including but not limited to gum arabic (or gum acacia), gum tragacanth, guar gum, locust bean gum, gum karaya, mesquite gum, galactomannans, pectine, soluble soybean polysaccharide)

Marine extracts such as carrageenan and alginate

Microbial and animal polysaccharides such as gellan, dextran, xanthan and chitosan Polysaccharides can be further classified according to their solubility in water. Particularly, cellulose is not soluble in water. According to the invention, the polysaccharides exhibit the ability to be soluble in water.

As used herein the term "ambient temperature" or "room temperature" means a temperature between 10° C. and 30° C., particularly between 20° C. and 25° C.

As used herein, the term "soluble" designates the ability of a solute (i.e, carrier, enzymes) to be dissolved in a liquid solvent. The solubility of a substance depends on the physical and chemical properties of both the solute and solvent, as well as temperature, pressure and pH of the solution and may be defined according to international standards such as IUPAC.

According to the IUPAC definition, the solubility is the analytical composition of a saturated solution expressed as a proportion of a designated solute in a designated solvent. Solubility may be stated in various units of concentration such as molarity, molality, mole fraction, mole ratio, mass (solute) per volume(solvent) and other units. Solubility is defined at a particular temperature and particular atmospheric pressure. The extent of solubility ranges widely, from infinitely soluble (without limit) or fully miscible, such as ethanol in water, to poorly soluble, such as silver chloride in water. The term insoluble is often applied to poorly or very poorly soluble solute. The term "maximum solubility" refers to the saturation concentration of the solute in the solvent, where an additional quantity of the solute does not increase the concentration of the solution and where the excess amount of solute begins to precipitate. According to the invention, the maximum solubility refers to the saturation concentration of the carrier in the liquid composition, wherein other components, such as the biological entities, may impact on the solute's solubility.

As used herein, the term "by weight" refers to a quantity based on the total weight of the considered composition or product.

In the context of the invention, the term "about" refers to a margin of +/−5%, preferably of +/−1%, or within the tolerance of a suitable measuring device or instrument.

Homogeneity of the Plastic Article

The inventors have shown that it is possible to improve the degradability and the physical and/or mechanical characteristics of plastic articles comprising polyester and biological entities having a polyester-degrading activity by the use of a liquid composition of biological entities with a specific polysaccharide carrier during the production process, compared to the use of solid or liquid compositions of biological entities in the art.

The inventors have found a way to reduce the surface roughness and eventually the thickness of the plastic article without going through heavy and expensive grinding operations of a solid composition. In addition, the pulverence of the constituents of said liquid composition is reduced as compared to solid composition and thus reduces the risks of inhalation of particles of the solid composition during the plastic article production process. The inventors have discovered that producing plastic article with the biological entities with a specific carrier, preferably in a liquid composition, leads to plastic articles with an increased homogeneity of the dispersion of biological entities in the plastic article compared to plastic articles produced with biological entities under a solid or liquid form of the art, thus leading to a plastic article with enhanced physical properties. The inventors have also discovered that the choice of the carrier is of importance in order to protect the biological entities during the production process and leads to plastic articles with expected degradation and technical performance.

It is therefore an object of the invention to provide a biodegradable plastic article, comprising at least one polyester and biological entities having a polyester-degrading activity, wherein the biological entities are able to degrade said polyester and are homogeneously dispersed in the plastic article.

It is also another object of the invention to provide a method for homogenizing the dispersion of polyester-degrading biological entities in a plastic article comprising at least one polyester and said biological entities, said method comprising introducing during the process of production of such plastic article, the biological entities with a specific carrier, preferably in a liquid composition.

The homogeneity of the dispersion of biological entities in the plastic article of the invention may be evaluated by the one skilled in the art, according to methods known per se in the art.

For instance, and within the context of the invention, the homogeneity of the dispersion of biological entities in the plastic article may be assessed by the measurement of at least one of the following properties: Haze, surface roughness, dynamic friction coefficient, Young's modulus, elongation at break, tensile stress at break, maximum stress, strain at maximum stress, impact strength and biodegradability.

Haze is defined as the percentage of incident light scattered by more than 2.5° through the plastic article. Haze is caused by impurities contained in the plastic article (such as accumulation of tiny particles in the article or very small defects on the surface) or its level of crystallinity. The lower the Haze value, the higher the clarity of the article is. Haze has no specific unit, it is expressed in %. If Haze value is greater than 30%, the article is diffusing. Hazemeters and spectrophotometers may be used to measure the level of Haze. Haze of plastic articles may be measured according to ASTM D1003 or NF EN 2155-9. According to the invention, the haze of the article is measured according to NF EN 2155-9 (August 1989).

Particularly, the plastic article of the invention produced from a liquid composition of biological entities may exhibit a lower haze value than the same plastic article produced from a solid composition of biological entities. Typically, the plastic article of the invention shows a Haze value reduced of about 1%, 2%, 3%, 4%, 5% or more, as compared to the Haze value of a plastic article produced with a solid composition of biological entities.

Young's modulus of the plastic article, also known as the elastic modulus or tensile modulus, is a measure of the stiffness of a solid material. It is a mechanical property of linear elastic solid materials. It defines the relationship between stress (force per unit area) and strain (proportional deformation) in a material. The result shall be expressed in pascal or megapascals (MPa).

Elongation at break or strain at break of the plastic article is related to the ability of a plastic article to resist changes of shape without cracking. Elongation at break is also known as fracture strain or tensile elongation at break. It is measured in % and can be calculated by dividing the extension at break of the plastic article by the initial gage length of the plastic article and multiplying by 100.

Tensile stress at break also known as stress at break or tensile strength at break of the plastic article is defined as the tensile stress at which the test specimen ruptures. Tensile stress also known as ultimate tensile stress or maximum stress corresponds to the maximum tensile stress sustained by the test specimen during tensile test. The result shall be expressed in force per unit area, usually megapascals (MPa).

Strain at maximum stress or tensile strain at tensile strength is the tensile strain at the point corresponding to the tensile strength. It is measured in % and can be calculated by dividing the extension at maximum stress of the plastic article by the initial gage length of the plastic article and multiplying by 100.

Young's modulus, elongation at break, tensile stress at break, maximum stress, strain at maximum stress, of plastic articles may be measured according to ASTM D882-12 or NF EN ISO 527-3 for plastic article with a thickness below 1 mm. It may particularly be measured in two different directions: machine direction or transverse direction. Determination of these criteria for plastic articles with a thickness from 1 mm to 14 mm is done with ASTM D638-14 or NF EN ISO 527-2.

Particularly, the plastic article of the invention obtained by the use of a liquid composition of biological entities may exhibit a higher elongation at break than the same plastic article produced from a solid composition of biological entities. Typically, the plastic article of the invention is a plastic film and shows an elongation at break, in at least one direction selected from machine direction or transverse direction, 10% higher, preferably 20%, 50%, 100% higher, or more, than the elongation at break of a plastic article produced with a solid composition of biological entities.

Particularly, the plastic article of the invention produced with a liquid composition of biological entities may exhibit a higher tensile stress at break than the same plastic article produced from a solid composition of biological entities. Typically, the plastic article of the invention is a plastic film and shows a tensile stress at break 20% higher, preferably 30%, 40%, 50% higher, or more, than the tensile stress at break of a plastic article produced with a solid composition of biological entities. Typically, the plastic article of the invention shows a tensile stress at break 5 MPa higher, preferably 7 MPa, 10 MPa, 15 MPa higher, or more, than the tensile stress at break of a plastic article produced from a solid composition of biological entities, in at least one direction selected from machine direction or transverse direction.

Particularly, the plastic article of the invention produced from a liquid composition of biological entities may exhibit a higher Young modulus than the same plastic article produced from a solid composition of biological entities. Typically, the plastic article of the invention is a plastic film and shows a Young modulus of about 20% higher, preferably 30%, 40%, 50% higher, or more, than the Young modulus of a plastic article produced from a solid composition of biological entities, in at least one direction selected from machine direction or transverse direction. Typically, the plastic article of the invention is a plastic film and shows a Young modulus of about 20 MPa higher, preferably 30 MPa, 50 MPa, 100 MPa higher, or more, than the Young modulus of a plastic article produced from a solid composition of biological entities, in at least one direction selected from machine direction or transverse direction.

Dynamic friction coefficient or sliding friction coefficient or coefficient of kinetic friction (also abbreviated as $\mu_D$) occurs when two objects are moving relative to each other and rub together (like a sled on the ground). According to the invention, $\mu_D$ is measured when a plastic article is sliding over another same plastic article. The sliding friction coefficient is defined as the ratio of the dynamic frictional force face by the plastic article (force needed to overcome friction) to the normal force N acting perpendicular to both plastic articles. The coefficient has no unit. The surfaces to be tested are placed in planar contact and under uniform contact pressure (normal force N). The force required to move the surfaces relative to each other is recorded (dynamic frictional force). According to the invention, $\mu_D$ is measured according to standard NF EN ISO-8295 (December 2004) which fits for plastic film or plastic sheet with a thickness below 0.5 mm. The apparatus comprises a horizontal test table on which is placed the plastic article of the invention, a mass generating the press force (1.96 N) and to which the plastic article is attached, and a traction mechanism for producing a relative movement between the mass and test table. According to the invention, the mass is pulled and moved on the test table (test speed=500 mm/min). The measure is precise about 0.01%. Particularly, the plastic article of the invention produced from a liquid composition of biological entities may exhibit a lower dynamic friction coefficient than the same plastic article produced from a solid composition of biological entities. Typically, the plastic article of the invention is a plastic film and shows a dynamic friction coefficient 5% lower, preferably 10%, 15%, 20% lower, or more, than the dynamic friction coefficient of a plastic article produced from a solid composition of biological entities.

Surface roughness of the plastic article may be assessed by a visual test of a panel of users. The plastic article of the invention shows no visible defects on its surface, it is smooth. The plastic article produced from a solid composition shows irregularity on the surface due to particles aggregates that we can feel by touch and visible to the naked eye. This is also assessed by the measurement of the thickness using a Mitutoyo thickness gauge to demonstrate the presence of aggregates in the plastic article.

Impact strength is defined as the resistance of a material to fracture under stress applied at high speed, defined by the amount of energy absorbed before fracture. For rigid plastic article, impact strength may be measured according to standard NF EN ISO 179 using plastic specimens produced with the same material of such plastic article and having thickness of 4 mm and a total length of 80 mm. Determination of impact strength for rigid plastic article with a thickness below 4 mm may also be measured directly on such plastic article according to standard NF EN ISO 6603-1. Particularly, the plastic article of the invention obtained by the use of a liquid composition of biological entities may exhibit a higher impact strength than the same plastic article produced from a solid composition of biological entities. Typically, the plastic article of the invention shows an impact strength of about 20% higher, preferably 25%, 30%, 40% higher than the impact strength of a plastic article produced from a solid composition of biological entities.

The inventors have also shown that the introduction of biological entities by way of the liquid or solid compositions comprising biological entities and a selected carrier, preferably by the way of the liquid composition, during the production process of a plastic article of the invention does not impact the technical performances of such plastic articles compared to plastic articles containing no biological entities.

The invention also provides a method for increasing the biodegradability of a plastic article of the invention, said method comprising introducing during the process of production of the plastic article, the composition of biological entities with a selected carrier. The biodegradability is further increased by the introduction during the process of production of the plastic article, of a liquid composition of biological entities with a selected carrier. Biodegradability of the plastic article is defined as the liberation of monomers, dimers, or water and carbon dioxide over a defined period of time under aqueous conditions. Particularly, according to the invention, the biodegradability of a plastic article containing PLA is measured according to the release of lactic acid and dimer of lactic acid. Particularly, the plastic article of the invention obtained by the use of a liquid composition of biological entities may exhibit a higher biodegradability than the same plastic article produced from a solid or liquid composition of biological entities of the art. Typically, the plastic article of the invention shows a biodegradability of about 100% higher, preferably 25%, 30%, 40% higher than the biodegradability of a plastic article produced from a solid or liquid composition of biological entities of the art after 2 days.

In a particular embodiment, the plastic article of the invention is a plastic film, comprising at least one polyester and biological entities able to degrade said polyester.

According to a preferred embodiment, the plastic film of the invention is a film with a thickness below 100 μm, preferably below 50 μm, more preferably below 30 μm, even more preferably below 20 μm.

Particularly, the plastic film of the invention shows a lower Haze value of about 3%, 4%, 5% or more, as compared to the haze value of a plastic film produced from a solid composition of biological entities. Accordingly, the plastic film Haze value is comprised between 80% and 95%, preferably between 85% and 93%. Alternatively, the plastic film Haze value is above 30%, preferably above 50%, more preferably above 70%, even more preferably above 85%. Otherwise, the plastic film Haze value is below 98%, preferably below 96%, more preferably below 95%, even more preferably below 94%. In another embodiment, the plastic film Haze value is below 60%.

In another particular embodiment, the film's Young's modulus is preferably above 200 MPa in both direction (machine or transverse), and/or the film's tensile stress at break is preferably above 15 MPa in both direction (machine or transverse), and/or the film's elongation at break is preferably above 130% in machine direction and above 300% in transverse direction. In another particular embodiment, the film according to the invention has an elongation at break greater than 130%, in longitudinal direction and greater than 240% crosswise, measured according to EN ISO 527-3, and/or a tear strength greater than 30 N/mm in the transverse direction of the film, measured according to EN ISO 6383-1 and this while having a high PLA content. It also has an elastic modulus greater than 200 MPa in the longitudinal direction and greater than 150 MPa transverse, measured according to EN ISO 527-3 and/or a maximum stress greater than 15 MPa in longitudinal direction and greater than 13 MPa in transverse direction, measured according to EN ISO 527-3.

In another particular embodiment, the plastic article of the invention is a rigid plastic article, comprising at least one polyester and biological entities having able to degrade said polyester.

In a particular embodiment, the rigid plastic article of the invention shows an impact strength above 17 kJ/m$^2$, preferably above 20 kJ/m$^2$ according to NF EN ISO 179. In another particular embodiment, the rigid plastic article of the invention shows, according to NF EN ISO 527-2, a tensile modulus below 4 GPa, preferably below 3 GPa, and the tensile strength at break is above 40 MPa, preferably above 55 MPa.

According to a particular embodiment, the rigid plastic article of the invention is a sheet with a thickness below 800 μm, preferably below 450 μm. The sheet of the invention shows an impact strength above 1 J, preferably above 1.5 J, more preferably above 2 J, according to NF EN ISO 7765-1. The elastic modulus of the sheet is below 2 GPa in both direction (machine and transverse) while maintaining enough stiffness for the intended application, and the strain at maximum stress of the sheet is above 3%, preferably above 4% in both direction.

In another particular embodiment, the plastic article of the invention is a nonwoven fabrics, comprising at least one polyester and biological entities having able to degrade said polyester.

Advantageously, the plastic article is a biodegradable plastic article complying with at least one of the relevant standards and/or labels known by a person skilled in the art such as standard EN 13432, standard NFT51800, standard ASTM D6400, OK Biodegradation Soil (Label TUV Austria), OK Biodegradation Water (Label TUV Austria), OK Compost (Label TUV Austria), OK Compost Home (Label TUV Austria).

A biodegradable plastic article refers to a plastic that is at least partially transformed under environmental conditions into oligomers and/or monomers of at least one polyester of the plastic article, water, carbon dioxide or methane and biomass. For instance, the plastic article is biodegradable in water. Preferably, about 90% by weight of the plastic article is biodegraded in water within less than 90 days, more preferably within less than 60 days, even more preferably within less than 30 days. More preferably, the plastic article may be biodegraded when exposed to wet and temperature conditions that occur in landscape.

Preferably, about 90% by weight of the plastic article is biodegraded with less than 3 years in the environment, more preferably within less than 2 years, even more preferably within less than 1 year. Alternatively, the plastic article may be biodegraded under industrial composting conditions, wherein the temperature is maintained above 50° C.

The invention also provides a method for increasing the biodegradability of a plastic article comprising at least one polyester, wherein the method comprises the step of mixing a polyester with both biological entities suitable for degrading said polyester and anti-acid filler to obtain a plastic composition and the step of manufacturing a plastic article with said plastic composition.

Components of the Plastic Article

It is an object of the invention to provide a plastic article, comprising at least one polyester, selected from copolymers of lactic acid and/or succinic acid and/or terephthalic acid or mix thereof.

Advantageously, the plastic article comprises at least one polyester selected from polylactic acid (PLA) (such as poly(L-lactic acid) (PLLA), poly(D-lactic acid) (PDLA), poly(D,L-lactic acid) (PDLLA) or PLA stereocomplex (sc-PLA)), polyglycolic acid (PGA), polyhydroxyalkanoate (PHA), polycaprolactone (PCL), polybutylene succinate (PBS), polybutylene succinate adipate (PBSA), polybutylene adipate terephthalate (PBAT), and derivatives or blends/mixtures thereof. In a preferred embodiment, the plastic article comprises at least PLA and/or PCL and/or PBAT, more preferably at least PLA. In another embodiment the polyester is selected from copolymers of lactic acid and/or succinic acid and/or terephthalic acid.

Preferably the polyester has a melting temperature above 140° C.

In another particular embodiment, the plastic article comprises at least two polyesters selected from polylactic acid (PLA), polyglycolic acid (PGA), polyhydroxyalkanoate (PHA), polycaprolactone (PCL), polybutylene succinate (PBS), polybutylene succinate adipate (PBSA), polybutylene adipate terephthalate (PBAT), and derivatives or blends/mixtures thereof. In a preferred embodiment, the plastic article comprises at least two polyesters selected from PLA and/or PCL and/or PBAT, more preferably from PLA and PBAT or from PLA and PCL.

In a particular embodiment, the plastic article may further comprise at least one natural polymer. Natural polymers may be selected from the group of lignin, polysaccharides such as cellulose or hemi-cellulose, starch, chitin, chitosan, and derivatives thereof or blends/mixtures thereof. In a particular embodiment, the natural polymers are plasticized (e.g., by a plasticizer such as water or glycerol) prior to their use for producing the masterbatch composition. Such plasticizing step modifies the chemical structure of the natural polymers allowing their use through a plastic production process. Preferably, the plastic article further comprises at least one natural polymer, selected from cellulose, starch, flour, gums and derivatives. More preferably, the plastic article of the invention further comprises at least starch or flour, even more preferably plasticized starch or flour.

Particularly the starch was plasticized by glycerol.

The plastic article of the invention further comprises a carrier selected among polysaccharides, a carrier polymer having a melting temperature below 140° C. and/or a glass transition temperature below 70° C. and mixtures thereof.

Preferably, the plastic article of the invention further comprises a polysaccharide carrier and optionally a carrier polymer having a melting temperature below 140° C. and/or a glass transition temperature below 70° C.

More preferably, the plastic article of the invention further comprises a polysaccharide carrier and a carrier polymer having a melting temperature below 140° C. and/or a glass transition temperature below 70° C.

The polysaccharide carrier is preferably selected from starch derivatives, natural gums, marine extracts, microbial and animal polysaccharides. Particularly, such polysaccharide is a starch derivative and is preferably maltodextrine. Alternatively, such polysaccharide is a natural gum and is preferably selected from arabic gum, guar gum, tragacanth gum, karaya gum, even more preferably from arabic gum. Alternatively, such polysaccharide is a marine extract and is preferably selected from carrageenan or alginate. Alternatively, such polysaccharide is a microbial polysaccharide and is preferably xanthan. Alternatively, such polysaccharide is an animal polysaccharide and is preferably chitosan.

In a particular embodiment, the carrier polymer having a melting temperature below 140° C. and/or a glass transition temperature below 70° C. is a polyester, preferably selected from polycaprolactone (PCL), poly butylene succinate adipate (PBSA), polybutylene adipate terephthalate (PBAT), polyhdroxyalkanoate (PHA), polylactic acid (PLA), or copolymers. In another particular embodiment, the carrier polymer is a natural polymer, preferably selected from starch. In another particular embodiment the carrier polymer is a "universal" polymer, i.e., a polymer that is compatible with a broad range of polymers, such as a copolymer (e.g. ethylene vinyl acetate copolymer EVA).

Preferably, the carrier polymer as defined above has a melting temperature below 120° C., and/or a glass transition temperature below 30° C. For instance, such carrier polymer is selected from the group consisting of PCL, PBAT, PLA and EVA. Preferably, the carrier polymer is selected from the group consisting of PCL, PBAT and PLA. The advantage of such embodiment is to reduce the heating of the biological entities during the masterbatch production process.

In a particular embodiment, the plastic article of the invention comprises PLA and at least one additional polyester selected from PBAT and/or PCL, and at least one natural polymer selected plasticized starch or flour.

According to another particular embodiment, the plastic article of the invention may further comprise one or more fillers. The filler can be selected from any conventional filler used in the plastic industry. The filler can be natural or synthetic. The filler can be selected from mineral or organic fillers. In a preferred embodiment, the mineral filler is chosen from the group consisting without limitation of calcite, carbonate salts or metal carbonate such as calcium carbonate (or limestone), potassium carbonate, magnesium carbonate, aluminium carbonate, zinc carbonate, copper carbonate, chalk, dolomite, silicate salts such as hydrous magnesium silicate such as talc or soapstone, calcium silicate (wollastonite), potassium silicate, magnesium silicates (talc), aluminium silicate (kaolin), or mix thereof such as mica, smectite such as montmorillonite, vermiculite, and palygorskite-sepiolite, sulphate salts such as barium sulfate, or calcium sulfate (gypsum), mica, hydroxide salt or metal hydroxide such as calcium hydroxide or potassium hydroxide (potash) or magnesium hydroxide or aluminium hydroxide or sodium hydroxide (caustic soda), hydrotalcite, metal oxide or oxide salts such as oxide of magnesium or oxide of calcium or oxide of aluminium or iron oxide or copper oxide, clay, asbestos, silica, graphite, carbon black, metal fibers or metal flakes, glass fibers, magnetic fillers, aramid fibers, ceramic fibers and derivatives thereof or blends/mixtures of these materials. In another preferred embodiment, the organic filler is chosen from the group consisting of wood flour, plant or vegetable flour such as cereal flour (corn flour, wheat flour, rice flour, soy bean flour, nutshell flour, clam shell flour, corn cob flour, cork flour, rice hull flour); saw dust; plant fibers such as flax fibers, wood fibers, hemp fibers, bamboo fibers, chicken feathers and derivatives thereof or blends/mixtures of these materials. Natural polymers can also be used as organic fillers, such as lignin, or polysaccharides such as cellulose or hemi-cellulose, starch, chitin, chitosan and derivatives or blends/mixtures of these materials. The type and exact quantity of fillers can be adapted by a person skilled in the art depending on the type of plastic article and following guidance provided in the present application. Advantageously, the plastic article comprises at least one filler selected from calcium carbonate, talc or silica.

According to another particular embodiment, the plastic article of the invention may further comprise one or more additives. Generally speaking, the additives are used in order to enhance specific properties in the final product (i.e., the final plastic article made with said masterbatch composition). For instance, the additives may be selected from the group consisting without limitation of plasticizers, coloring agents, processing aids, slip additives, rheological agents, anti-static agents, anti-UV agents, toughening agents, impact modifiers, anti-fogging agents, compatibilizers, flame retardant agents, anti-oxidants, light stabilizers, oxygen scavengers, inks, adhesives, fertilizers, and phytosanitary products. Advantageously, the plastic article comprises at least one additive selected from plasticizers, slip additives and light stabilizers. Advantageously, the plastic article comprises less than 20% by weight of such additives, preferably less than 10%, more preferably less than 5%, typically between 0.1 and 4% by weight of such additives.

Advantageously, the plastic article of the invention comprises, based on the total weigh of the plastic article:
- from 10 to 98% of a polyester as defined above, particularly polylactic acid (PLA),
- from 0.01 to 10% of a polysaccharide carrier, as defined above,
- from 0 to 30% of a carrier polymer having a melting temperature below 140° C. and/or a glass transition temperature below 70° C., as defined above and
- from 0.01 to 10% of biological entities having a PLA-degrading activity.

Preferably the plastic article comprises at least 3% of a carrier polymer, more preferably at least 4% of a carrier polymer. In another preferred embodiment, the plastic article comprises from 0.1% to 1% of polysaccharide carrier. In another preferred embodiment, the plastic article comprises less than 1% of biological entities having a PLA-degrading activity, preferably less than 0.5%, preferably about 0.25%.

In a particular embodiment, the plastic article comprises from 0.1 to 0.5% of enzymes having a PLA-degrading activity, preferably about 0.25%.

In a particular embodiment, the plastic article of the invention comprises, based on the total weigh of the plastic article:
- from 10 to 94% of a polyester as defined above, particularly polyactic acid (PLA),
- from 0.1 to 5% of a polysaccharide carrier, as defined above,
- from 4 to 20% of a carrier polymer having a melting temperature below 140° C. and/or a glass transition temperature below 70° C., as defined above and
- from 0.01 to 1% of biological entities having a PLA-degrading activity.

Other compositions of the invention are described here below. Although not mentioned, they all fulfill the characteristic that they all include in addition less than 5% of a polysaccharide carrier as defined above, particularly between 0.1 to 1% of a polysaccharide carrier.

and that the second polyester and/or the natural polymer can correspond to the carrier polymer or to additional polymer. Additionally, a carrier polymer as defined previously may also be included and can be referred as a second polyester or a third polyester.

In a particular embodiment, the plastic article of the invention comprises, based on the total weigh of the plastic article:
- from 10 to 98% of PLA
- from 0 to 70% of a second polyester
- from 0 to 40% of natural polymer
- from 1 to 20% of additives
- from 0 to 40% of at least one filler
- from 0.01 to 10% of biological entities having a PLA-degrading activity In a particular embodiment, the plastic article of the invention comprises, based on the total weigh of the plastic article:
- from 10 to 98% of PLA
- from 0 to 50% of a second polyester, preferably selected from PBAT
- from 0.1 to 10% of a third polyester, preferably selected from a polymer with a melting temperature below 140° C.
- from 0 to 40% of natural polymer
- from 1 to 20% of additives
- from 0 to 40% of at least one filler
- from 0.01 to 10% of biological entities having a PLA-degrading activity In a particular embodiment, the plastic article is a plastic film. Preferably, the plastic film of the invention comprises, based on the total weigh of the plastic film:
- from 10 to 60% of PLA, preferably from 20 to 40%
- from 10 to 60% of a second polyester, preferably selected from PBAT, preferably from 20 to 40%
- from 0 to 40% of natural polymer, preferably selected from starch, preferably from 0 to 30% from 1 to 20% of additives, preferably selected from plasticizers or compatibilizers from 0.1 to 10% of at least one filler, preferably selected from calcium carbonate from 0.01 to 10% of biological entities having a PLA-degrading activity In another particular embodiment, the plastic film of the invention comprises, based on the total weigh of the plastic film:

from 10 to 60% of PLA, preferably from 20 to 40% from 10 to 60% of a second polyester, preferably selected from PBAT, preferably from 20 to 40% from 1 to 20% of additives, preferably selected from plasticizers or compatibilizers from 0.01 to 10% of biological entities having a PLA-degrading activity In another particular embodiment, the plastic film of the invention comprises, based on the total weigh of the plastic film:

from 10 to 60% of PLA, preferably from 20 to 40% from 10 to 60% of a second polyester, preferably selected from PBAT, preferably from 20 to 40% from 0 to 10% of a third polyester from 1 to 20% of additives, preferably selected from plasticizers or compatibilizers from 0.01% to 10% of biological entities having a PLA-degrading activity In another particular embodiment the plastic film of the invention comprises, based on the total weigh of the plastic film:

from 10 to 60% of PLA, preferably from 20 to 40% from 10 to 60% of a second polyester, preferably selected from PBAT, preferably from 20 to 40% from 0 to 10% of a third polyester, preferably selected from PCL from 1 to 40% of natural polymer, preferably selected from starch, preferably from 10 to 30% from 1 to 20% of additives, preferably selected from plasticizers or compatibilizers from 0.1 to 10% of at least one filler, preferably selected from calcium carbonate from 0.01 to 10% of biological entities having a PLA-degrading activity In a particular embodiment, the film of the invention has a thickness between 15 µm and 30 µm and comprises at least from 10% to 40% of PLA based on the total weigh of the plastic film, from 5% to 15% of PCL, from 40% to 70% of PBAT. Such film, advantageously has a higher depolymerization rate than a film without polysaccharide carrier and/or carrier polymer as PCL. while maintaining a good elongation at break regarding the application, above 140% in MD.

In a particular embodiment, the rigid plastic article of the invention comprises, based on the total weigh of the plastic article:

from 10 to 98% of PLA from 0 to 60% of a second polyester from 0 to 20% of additives from 0 to 40% of at least one filler from 0.01 to 10% of biological entities having a PLA-degrading activity In a preferred embodiment, the plastic article of the invention is produced from a rigid plastic sheet of the invention. Preferably, the rigid plastic sheet of the invention comprises, based on the total weigh of the plastic article:

from 10 to 98% of PLA, preferably from 50 to 95% from 0 to 30% of a second polyester, preferably selected from PCL which improve impact strength from 0 to 20% of additives, preferably selected from plasticizers, impact modifier and nucleating agent from 0 to 40% of at least one filler, preferably selected from calcium carbonate from 0.01 to 10% of biological entities having a PLA-degrading activity In a particular embodiment, the rigid plastic article of the invention comprises, based on the total weigh of the plastic article:

from 10 to 98% of PLA from 0 to 50% of a second polyester from 0 to 20% of a third polyester from 0 to 40% of natural polymer from 0 to 20% of additives from 0 to 40% of at least one filler from 0.01 to 10% of biological entities having a PLA-degrading activity In a particular embodiment, the rigid plastic article of the invention comprises more than 90% of PLA based on the total weigh of the plastic article, and exhibits an impact strength above 1 J. In another particular embodiment, the plastic article of the invention is obtained by the use of a liquid composition of biological entities and from a master-batch comprising 80% of PCL. Thus, this plastic article contains at least 4% of PCL and exhibit an impact strength above 2 J and an elongation at break above 6% preferably above 15% with maintaining a good stiffness regarding the application, above 1.6 GPa.

Biological Entities

According to the invention, the plastic article comprises biological entities suitable for degrading at least one polyester contained in said plastic article. In another particular embodiment, the plastic article comprises biological entities suitable for degrading at least two polyesters contained in said plastic article.

In a preferred embodiment, the biological entities comprise at least an enzyme with polyester-degrading activity and/or at least a microorganism expressing, and optionally excreting, an enzyme having a polyester-degrading activity. In a preferred embodiment, the biological entities consist in at least an enzyme with polyester-degrading activity. In another particular embodiment, the biological entities comprise or consist in at least two enzymes with polyester-degrading activity. Examples of suitable enzymes having a polyester-degrading activity for use in the invention include, without limitation, depolymerase, esterase, lipase, cutinase, carboxylesterase, protease, or polyesterase. In a particular embodiment, the biological entities comprise or consist in an enzyme with a PLA-degrading activity. The biological entities is a protease, preferably selected from *Amycolatopsis* sp., *Amycolatopsis orientalis*, proteinase K from *Tritirachium album, Actinomadura keratinilytica, Laceyella sacchari* LP175, *Thermus* sp., *Bacillus licheniformis, Bacillus thermoproteolyticus* or any commercial enzymes known for degrading PLA such as Savinase®, Esperase®, Everlase®, Protex®, Optimase®, Multifect® or any enzymes from the family of the subtilisin CAS 9014-01-1 or any functional variant thereof.

The enzymes may be in pure or enriched form, or in mixture with other excipients or diluents. A combination of enzymes may be used as well.

In an alternative embodiment, the biological entities comprise microorganisms that produce such enzymes, either naturally or as a result of particular engineering (e.g., recombinant microorganisms). Preferred examples of suitable microorganisms include, without limitation, bacteria, fungi and yeasts. In an embodiment, the biological entities comprise sporulating microorganisms and/or spores thereof.

In a particular embodiment, the biological entities comprise enzymes encapsulated in nanocapsules, enzymes encapsulated in cage molecules, and enzymes aggregated together. The term "cage molecule" designates a molecule that can be inserted into the structure of said enzymes to stabilize them and to make them resistant to high temperatures. Encapsulation techniques are well known to those skilled in the art and include, for instance, nanoemulsions.

In a particular embodiment, the plastic article comprises less than 11% by weight, preferably between 0.01% and 10% by weight of biological entities, based on the total weight of the plastic article.

The biological entities may be supplied in a liquid or solid form. For instance, the biological entities may be in a powder form. In a particular embodiment, the biological entities used to prepare the plastic article are a liquid composition of enzymes and/or microorganisms mixed with a diluent or carrier, such as stabilizing and/or solubilizing component(s). For instance, the composition may be a solution comprising enzymes and/or microorganisms in suspension in water, and optionally additional components, such as glycerol, sorbitol, dextrin, starch, glycol such as propanediol, salt, etc.

According to the invention, the biological entities used to prepare the plastic article are supplied under a liquid composition comprising said biological entities having a polyester-degrading activity, a carrier and an aqueous solvent, wherein the carrier is a polysaccharide selected from starch derivatives, natural gums, marine extracts, microbial and animal polysaccharides.

Process for Producing the Plastic Article

The invention also provides for a process for preparing a plastic article comprising at least one polyester and biological entities having a polyester-degrading activity homogeneously dispersed in the plastic article, said process comprising a step (a) of mixing between 0.01% and 10% by weight of biological entities having a polyester-degrading activity with a least said one polyester and a step (b) of shaping said mixture of step (a) in a plastic article, wherein the biological entities are mixed during step (a) under a form appropriate for allowing homogeneous dispersion of the said biological entities in the plastic article, said form being selected among
  a liquid composition comprising the biological entities having a polyester-degrading activity, a polysaccharide carrier and water, or
  a masterbatch comprising the biological entities having a polyester-degrading activity and a carrier polymer having a melting temperature below 140° C. and/or a glass transition temperature below 70° C.

Preferably the step (a) of mixing is performed at a temperature at which the polyester is in a partially or totally molten state and/or in an extruder.

Polyester, biological entities and carriers are defined above and in the examples as well as their proportions in the plastic article, the person skilled in the art being able to adjust the proportion of each of the ingredients to be used in the process to obtain such final proportions.

Liquid Composition

In a first embodiment, the biological entities are provided in the form of a liquid composition.

Preferably, the liquid composition comprises, based on the total weight of the composition:
  from 0.01% to 35% by weight of biological entities
  from 15% to 95% by weight of an aqueous solvent
  from 3% to 80% by weight of a polysaccharide carrier Particularly, the biological entities retain a polyester degrading activity of in the plastic composition and/or in the final plastic article.

The liquid composition is suitable to be extruded with a polymer. Preferably, the composition is suitable to be extruded with a synthetic polymer such as polyolefins, aliphatic or aromatic polyesters, polyamides, polyurethanes and polyvinyl chloride, or a natural polymer such lignin and polysaccharides, such as cellulose, hemi-cellulose, starch and derivatives thereof.

In a preferred embodiment, the composition is suitable to be extruded with a polymer with a low melting temperature or melting point (Tm), i.e. with a Tm below 140° C.

In a preferred embodiment, the aqueous solvent is water. In such embodiment, the composition comprises, based on the total weight of the composition, from 15% to 95% of water, and from 5% to 85% of other components, such as, at least, from 0.01% to 35% of biological entities and from 3% to 80% of a carrier.

In a particular embodiment, the liquid composition comprises, based on the total weight of the composition:
  from 0.3% to 30% by weight of biological entities
  from 19% to 85% by weight of an aqueous solvent
  from 4% to 80% by weight of a polysaccharide carrier In a preferred embodiment, the liquid composition comprises less than 35% by weight of biological entities. In another particular embodiment, the composition comprises less than 30% by weight of biological entities In another particular embodiment, the composition comprises less than 20% by weight of biological entities.

In preferred particular embodiment, the liquid composition comprises less than 80% by weight of aqueous solvent, preferably less than 75%, less than 70%, even more preferably less than 60%, based on the total weight of the composition. In another preferred embodiment, the composition comprises more than 20% by weight of aqueous solvent, preferably more than 30%, and less than 80%, based on the total weight of the composition.

In another particular embodiment, the composition comprises from 20% to 80% by weight of aqueous solvent, preferably from 30% to 75%, more preferably from 40% to 60%. In another particular embodiment, the composition comprises about 50% of aqueous solvent. In another particular embodiment, the composition comprises about 40% of aqueous solvent.

In a preferred embodiment, the aqueous solvent is water. In a preferred embodiment, the liquid composition comprises less than 75% by weight of water, preferably less than 70%, more preferably less than 60%, based on the total weight of the composition. In another preferred embodiment, the composition comprises more than 20% by weight of water, preferably more than 30%, and less than 80%, based on the total weight of the composition.

In another particular embodiment, the composition comprises from 20% to 80% by weight of water, preferably from 30% to 75%, more preferably from 40% to 60%. In another particular embodiment, the composition comprises about 50% of water. In another particular embodiment, the composition comprises about 40% of water.

In preferred particular embodiment, the liquid composition comprises more than 5% by weight of polysaccharide carrier, preferably more than 10%, even more preferably more than 15%.

Thus, in a preferred embodiment, the composition comprises, based on the total weight of the composition:
  From 0.3% to 30% by weight of biological entities From 19% to 60% by weight of an aqueous solvent From 15% to 70% by weight of a polysaccharide carrier In another preferred embodiment, the composition comprises less than 70% by weight of carrier, preferably less than 60%. In a particular embodiment, the composition comprises from 5% and 70% of carrier, preferably from 10% to 60%. In another particular embodiment, the composition comprises from 10% to 50% of carrier.

In another particular embodiment, the composition comprises, based on the total weight of the composition:
from 0.01% to 35% of biological entities
from 30% to 75% of water
from 10% to 69.99% of a carrier In another particular embodiment, the composition comprises, based on the total weight of the composition:
from 0.01% to 35% of biological entities
from 30% to 60% of water
from 20% to 45% of a carrier In another particular embodiment, the composition comprises, based on the total weight of the composition:
from 0.01% to 35% of biological entities
from 40% to 60% of water
from 20% to 45% of a carrier In another particular embodiment, the composition comprises about 50% of water, and from 0.01% to 35% of biological entities, and from 20% to 50% of carrier.

In another particular embodiment, the composition comprises about 40% of water, and from 0.01% to 35% of biological entities, and from 20% to 60% of carrier.

In a particular embodiment, the ratio polysaccharide carrier/aqueous solvent by weight is below 4.

In a particular embodiment, the quantity of polysaccharide carrier in the composition is from 4% to 100% of the maximum solubility of the carrier in the aqueous solvent, i.e., from 4% to 100% of the saturation concentration of the carrier in the aqueous solvent.

Alternatively or in addition, the quantity of polysaccharide carrier in the composition is from 4% to 100% of the maximum solubility of the carrier in the composition, i.e., from 4% to 100% of the saturation concentration of the carrier in the composition.

According to the invention, the presence of polysaccharide carriers in the composition allows to protect and stabilize the biological entities not only in the composition but also during a heat treatment, such as an extrusion process wherein the composition is introduced into a partially or totally molten polymer.

In a particular embodiment, the carrier is in a solid form at ambient temperature.

Advantageously, the carrier is also soluble in aqueous solvent such as water at ambient temperature. Preferably, the carrier is soluble in the liquid composition, at least at ambient temperature. Alternatively or in addition, the carrier is soluble in the liquid composition at a temperature of about 100° C.

In a particular embodiment, the carrier is a starch derivative. Preferably the carrier is maltodextrin. In such particular embodiment, the ratio by weight of maltodextrin/aqueous solvent is preferably between 3 and 4. In a particular embodiment, the quantity of maltodextrin in the composition is from 5 to 100% of its maximum solubility in the composition, preferably from 26 to 100%, more preferably from 39 to 100%. Accordingly, the composition comprises more than 4% by weight of maltodextrin, based on the total weight of the composition, preferably more than 20%, preferably more than 30%.

In a particular embodiment, the carrier is a natural gum. Preferably the carrier is selected from arabic gum, guar gum, tragacanth gum, karaya gum, more preferably the carrier is arabic gum. In a particular embodiment, the ratio by weight arabic gum/aqueous solvent is between 0.1 and 1, preferably between 0.3 and 0.8, more preferably between 0.35 and 0.6, even more preferably between 0.4 and 0.5. In another preferred embodiment, the ratio by weight arabic gum/aqueous solvent is above 0.8, preferably between 0.8 and 1. Particularly, the quantity of Arabic gum in the composition is from 6% to 100% of its maximum solubility in the composition, preferably from 40% to 100% of its maximum solubility, preferably from 60% to 100% of its maximum solubility. In another particular embodiment, the composition comprises more than 4% by weight of Arabic gum, preferably more than 10%, more preferably more than 15%, even more preferably more than 20%. In another particular embodiment, the composition comprises less than 70% by weight of Arabic gum, preferably less than 60%. In a particular embodiment, the composition comprises from 5% and 70% of Arabic gum, preferably from 10% to 60%. In another particular embodiment, the composition comprises from 10% to 50% of Arabic gum.

In another particular embodiment, the carrier is a marine extract. Preferably the carrier is selected from carrageenan or alginate.

In another particular embodiment, the carrier is a microbial polysaccharide. Preferably the carrier is xanthan.

In another particular embodiment, the carrier is an animal polysaccharide. Preferably the carrier is chitosan.

In a particular embodiment, the liquid composition comprises at least two carriers selected from starch derivatives, natural gums, marine extracts, microbial and animal polysaccharides. In another particular embodiment, the ratio carrier/biological entities is between 0.8 and 1.2, preferably about 1. In another particular embodiment, the ratio carrier/biological entities is above 1, preferably above 2. According to the invention, the liquid composition may further comprise sugars, proteins, lipids, organic acids, salts and vitamins originating from the culture supernatant of a polyester-degrading microorganism used as biological entities in the composition. Such supernatant may be preliminary treated (e.g., mechanically or physically or chemically) to increase the concentration of enzymes and/or to remove other components such as DNA or cell debris.

In a particular embodiment, the composition may further comprise polyols, such as glycerol, sorbitol or propylene glycol. This is particularly the case when producing the composition of the invention with commercial biological entities, preferably commercial enzymes, conditioned in a stabilizing solution comprising polyols. According to a particular embodiment, the composition comprises at most 10% by weight of polyols based on the total weight of the composition, preferably at most 5%. According to another particular embodiment, the composition comprises between 10% and 20% by weight of polyols based on the total weight of the composition.

According to a particular embodiment, the liquid composition may comprise non-soluble components with a particle size below 20 μm.

Alternatively or in addition, the composition further comprises mineral components such as calcium components that are known to increase the thermostability of some biological entities such as calcium carbonate, calcium chloride or other calcium minerals.

Advantageously, the liquid composition of the invention is stable, i.e chemically and biologically stable. In the context of the invention, "chemically stable" refers to a composition wherein the biological entities do not show any significant loss of activity during a defined period at room temperature, in the dark. More particularly, "chemically stable" refers to a composition wherein the loss of degrading activity of the biological entities is less than 50%, preferably less than 25%, more preferably less than 10% as compared to the degrading activity of said biological entities before introduction in the composition, during a period of time of at least 30 days, preferably at least 90 days, more preferably at least 1 year.

According to the invention, the composition of the invention is chemically stable during at least 90 days at 4° C. Particularly, the loss of degrading activity of the biological entities in the composition of the invention is less than 10% as compared to the degrading activity of said biological entities before introduction in the composition, during a period of time of at least 90 days. In the context of the invention, the term "biologically stable" refers to a composition that does not show any subsequent bacterial, yeast of fungal proliferation during a defined period of at least 30 days, preferably at least 90 days, more preferably at least 1 year, at room temperature, in the dark. Particularly, the composition further comprises antifungal and/or antibacterial components, such as sorbic acid and/or salts thereof, benzoic acid and salts thereof, sulfurous anhydride or sulfite, nitrate or nitrite, propionic acid, butyric acid, natamycin, paraben, acetic acid, citric acid, boric acid, vegetal extracts.

In another particular embodiment, the composition comprises, based on the total weight of the composition:
  from 0.01% to 35% of PLA-degrading enzymes
  from 30% to 75% of water
  from 10% to 69.99% of Arabic gum In another particular embodiment, the composition comprises, based on the total weight of the composition:
  from 0.01% to 35% of PLA-degrading enzymes
  from 30% to 60% of water
  from 20% to 45% of Arabic gum In another particular embodiment, the composition comprises, based on the total weight of the composition:
  from 0.01% to 35% of PLA-degrading enzymes
  from 40% to 60% of water
  from 20% to 45% of Arabic gum In another particular embodiment, the composition comprises about 50% of water, and from 0.01% to 35% of PLA-degrading enzymes, and from 20% to 50% of Arabic gum.

In another particular embodiment, the composition comprises about 40% of water, and from 0.01% to 35% of PLA-degrading enzymes, and from 20% to 60% of Arabic gum.

All the compositions set above optionally comprises from 0% to 20% of other components, preferably selected from proteins, salts, polyols, preferably from 0% to 5%. Additionally, the PLA-degrading enzymes of such compositions are preferably selected from proteases.

In a particular embodiment, the liquid composition of the invention comprises, based on the total weight of the composition:
  From 20% to 80% by weight of water, preferably from 40% to 60% of water
  From 0.01% to 30% by weight of PLA-degrading enzymes, preferably from 5% to 30% of protease
  From 10% to 50% by weight of arabic gum, preferably from 15% to 35%

In a particular embodiment, the composition of the invention comprises, based on the total weight of the composition:
  From 20% to 80% by weight of water, preferably from 40% to 60% of water
  From 0.01% to 30% by weight of PLA-degrading enzymes, preferably from 5% to 30% of protease
  From 10% to 50% by weight of arabic gum, preferably from 15% to 35%
  From 0% to 20% by weight of other components, preferably selected from proteins, salts, polyols In a particular embodiment, the composition of the invention comprises, based on the total weight of the composition:
  From 20% to 80% by weight of water, preferably from 40% to 60% of water
  From 0.01% to 30% by weight of PLA-degrading enzymes, preferably from 5% to 30% of protease
  From 10% to 50% by weight of maltodextrine, preferably from 15% to 40%

In a particular embodiment, the composition of the invention comprises, based on the total weight of the composition:
  From 20% to 80% by weight of water, preferably from 40% to 60% of water
  From 0.01% to 30% by weight of PLA-degrading enzymes, preferably from 5% to 20% of protease
  From 10% to 50% by weight of maltodextrine, preferably from 15% to 40%
  From 0% to 20% of other components, preferably selected from proteins, salts, polyols.

Advantageously, the liquid composition is in a liquid form at least at ambient temperature.

Preferably, the liquid composition is in a liquid form at the temperature at which said composition is introduced in a polymer which is in partially or totally molten state.

Advantageously, in all compositions stated above, the quantity of carrier and biological entities are expressed as dry matter, i.e. the quantity after full dehydration or water evaporation or water removing.

Masterbatch

In a particular embodiment, a liquid composition of biological entities is introduced in a first carrier polymer that has a low melting point (below 140° C., preferably below 120° C.) and/or a low glass transition temperature (below 70° C.), such as PCL, PBSA, PBAT to prepare a masterbatch. The resulting masterbatch is then added to a second polyester that has a high melting point, particularly PLA. For instance, the liquid composition is added to PCL that has been heated at about 70° C. to be in partially molten state. Then, the mixture is directly added to PLA that was heated to about 150° C. to be in a partially molten state. Alternatively, the mixture may be cooled and optionally conditioned before to be added to the second polyester during melting, at least partially.

The masterbatch in molten or solid form is also part of the invention.

The invention thus provides for a masterbatch comprising biological entities having a polyester-degrading activity and a carrier polymer having a melting temperature below 140° C. and/or a glass transition temperature below 70° C.

Biological entities and carrier polymer are defined above and in the examples and all definitions and precision on the nature, compositions and properties of said components defined for the plastic article applies also to the definition of the masterbatch.

The masterbatch particularly comprises from 50% to 95% by weight of carrier polymer based on the total weight of the masterbatch, preferably from 70% to 90% by weight of carrier polymer.

The masterbatch advantageously comprises from 5% to 50% by weight of biological entities composition based on the total weight of the masterbatch, more from 10% to 30% of biological entities composition.

The masterbatch is advantageously prepared with a liquid composition of the biological entities comprising a polysaccharide carrier as defined above.

Therefore, the masterbatch of the invention also comprises a polysaccharide carrier as defined above. Particularly it comprises from 1% to 30% of polysaccharide carrier based on the total weight of the masterbatch, preferably from 1% to 15%.

Advantageously, the residence time of the liquid composition and thereby of the biological entities in the carrier polymer at a temperature above 100° C. is as short as possible and preferably comprised between 5 seconds and 10 minutes, more preferably less than 5 minutes, 3 minutes, 2 minutes.

Below are descriptions of processes for preparing a plastic article as described above using a masterbatch, with or without a step where the masterbatch is in a solid state, conditioned for further use in a method for making an article according to the invention. The carrier polymer may be also identified as "first polymer". In describing the masterbatch, its preparation and use, the definitions, precisions, properties of the carrier polymer are the same for the first polymer.

For instance, the process comprises the steps of:

a) preparing a masterbatch comprising polyester-degrading biological entities and a carrier polymer by (i) heating the carrier polymer; and (ii) introducing from 5% to 50% by weight of biological entities based on the total weight of the masterbatch during heating of the carrier polymer; and (b) introducing the masterbatch in a polyester-based matrix during production of the plastic article wherein step a) is performed at a temperature at which the carrier polymer is in a partially or totally molten state and wherein biological entities are able to degrade the polyester of the polyester-based matrix and are introduced during step (ii) under the form of a liquid composition defined above, and step b) is performed at a temperature at which both the first polymer and the polyester of the polyester-based matrix are in a partially or totally molten state.

The step (a) of preparing the masterbatch may thus be performed at a temperature at or above 40° C., particularly at or above 45° C., 55° C., 60° C., 70° C., 80° C., 90° C., 100° C., or even above 150° C., depending on the nature of the first polymer. Typically, this temperature does not exceed 300° C. More particularly, the temperature does not exceed 250° C. Even more particularly, the temperature does not exceed 200° C. Step (a) is performed using a carrier polymer with low melting point, i.e. with a melting point below 140° C. and/or a low glass transition temperature (below 70° C.). For instance, step (a) is performed using PCL, PBAT or PBSA. The temperature of the mixing step can be adapted by a person skilled in the art depending on the type of polymer, and/or biological entities used for the production of the masterbatch. Particularly, the temperature is chosen according to the melting point, or melting temperature of the first polymer. In a particular embodiment, step (a) is performed at the melting point of the first polymer. The polymer is then in a partially or totally molten state.

In another embodiment, step (a) is performed at a temperature above the glass transition temperature of said polymer, particularly between the glass transition temperature (Tg) and the melting temperature of said polymer. In another particular embodiment, the step (a) of mixing is performed at a temperature above the melting temperature of said polymer.

According to the invention, the carrier polymer is heated at a temperature below 140° C., and the biological entities are introduced into the first polymer during said heating step. More generally speaking, the step of preparation of the masterbatch (step a) is performed at a temperature at which the first polymer is in a partially or totally molten state, so that the biological entities are embedded into the first polymer during the extrusion. Preferably, step a) is performed by extrusion.

In preferred embodiment, the masterbatch is prepared by (i) extruding a carrier polymer, wherein said carrier polymer has a melting temperature below 140° C. and (ii) introducing the biological entities during extrusion of the first polymer, before to introduce said masterbatch into a polyester-based matrix in order to prepare the plastic article.

In a particular embodiment, the carrier polymer is a polyester, preferably selected from polycaprolactone (PCL), poly butylene succinate adipate (PBSA), polybutylene adipate terephthalate (PBAT), polyhdroxyalkanoate (PHA), polylactic acid (PLA), or copolymers. In another particular embodiment, the first polymer is a natural polymer, preferably selected from starch. In another particular embodiment, the masterbatch comprises a "universal" polymer, i.e., a polymer that is compatible with a broad range of polymers, such as a copolymer (e.g. ethylene vinyl acetate copolymer EVA).

The masterbatch comprises a first polymer that has a melting temperature below 140° C. and/or a glass transition temperature below 70° C. Preferably, the first polymer of the masterbatch has a melting temperature below 120° C., and/or a glass transition temperature below 30° C. For instance, such first polymer is selected from the group consisting of PCL, PBAT, PLA and EVA. Preferably, such first polymer is selected from the group consisting of PCL, PBAT and PLA. The advantage of such embodiment is to reduce the heating of the biological entities during the masterbatch production process.

The masterbatch comprises between 5% and 50% by weight of biological entities, based on the total weight of the masterbatch, wherein the biological entities are supplied under the form of the liquid composition set above. Preferably, the biological entities represent between 10% and 40% by weight, more preferably between 10% and 30% by weight, based on the total weight of the masterbatch. In a particular embodiment, the masterbatch comprises about 20% by weight of the composition of biological entities. In a particular embodiment, the polyester-degrading biological entities are able to degrade the first polymer. Alternatively or in addition, the polyester-degrading biological entities are able to degrade at least one polyester of the final plastic article that incorporates the masterbatch.

The masterbatch may further comprise one or several additional compounds. In particular, the masterbatch may further comprise one or more additives. Generally speaking, the additives are used in order to enhance specific properties in the final product. For instance, the additives may be selected from the group consisting without limitation of plasticizers, coloring agents, processing aids, rheological agents, anti-static agents, anti-UV agents, toughening agents, impact modifiers, compatibilizers, slip additives, flame retardant agents, anti-oxidants, pro-oxidants, light stabilizers, oxygen scavengers, adhesives, products, excipients, slip additives. Advantageously, the masterbatch comprises less than 20% by weight of such additives, preferably less than 10%, typically between 0.1 and 10% by weight of such additives, based in the total weight of the masterbatch.

Preferably, the masterbatch comprises at least one additive selected from plasticizers, slip additives and light stabilizers.

Particularly, the masterbatch may further comprise at least one filler. The filler can be selected from any conventional filler used in the plastic industry. The type and exact quantity of fillers can be adapted by a person skilled in the art depending on the type of masterbatch composition. Advantageously, the masterbatch comprises at least one filler selected from anti-acids filler such calcium carbonate, talc or silica.

In a particular embodiment, the masterbatch composition comprises, based on the total weight of the masterbatch:
from 50 to 95% by weight of a carrier polymer;
from 5 to 50% by weight of polyester-degrading biological entities; and optionally
at least one additive.

In another particular embodiment, the masterbatch comprises, based on the total weight of the masterbatch:
from 70 to 90% by weight of a carrier polymer;
from 10 to 30% by weight of polyester-degrading biological entities; and optionally
at least one additive.

In a particular embodiment, the masterbatch is produced by a process called "compounding", usually an extrusion-granulation process, in which the first polymer is melted and mixed with the biological entities. Compounding combines mixing and blending techniques during a heat process, in order to ensure uniformity, homogeneity and dispersion in the masterbatch. The compounding is a technique known by a person skilled in the art.

Such compounding process may be carried out with an extruder, such as single-screw extruders, multi-screw extruders of either co-rotating or counter-rotating design, dispersive kneaders, reciprocating single-screw extruder (co-kneaders).

More generally, the step (a) of preparing the masterbatch may be carried out with an extruder, wherein the first polymer is heated, melted and mixed with the biological entities.

The first polymer may be introduced in the extruder in a powder or granulated form, preferably in a granulated form.

In a preferred embodiment, the extruder used for the production of the masterbatch of step (a) is a multi-screw extruder, preferably a twin-screw extruder, more preferably a co-rotative twin-screw extruder. In a particular embodiment, the extruder further comprises, after the screws, a static mixer. In another embodiment, the extruder is used with a die pierced with holes, preferably a least a two holes die. One skilled in the art will easily adapt the characteristics of the die (e.g. the number and size of the holes . . . etc), to the pressure, the output or the masterbatch intended.

In a preferred embodiment, the residence time of the mixture of first polymer and drug in the extruder is comprised between 5 seconds and 3 minutes, preferably is less than 2 minutes. When the masterbatch comprises a polymer with a melting temperature below 120° C., the residence time of the mixture in the extruder is comprised between 5 seconds and 10 minutes, preferably less than 5 minutes.

One skilled in the art will easily adapt the characteristics of the extruder (e.g., the length and diameter of the screw(s), the screw profile, degassing zones, etc.), and the residence time to the first polymer, the biological entities and the type of masterbatch intended.

As disclosed above, the biological entities are preferably introduced in the extruder under the form of a liquid composition described above.

Particularly, such extruder may contain a principal hopper and several successive heating zones, wherein the temperature may be independently controlled and regulated and wherein additional components may be added at different time during the process. Vacuum and natural degassing zone are necessary during the extrusion to remove the volatile products like water.

The liquid composition of biological entities is introduced with a pump. In a particular embodiment, the biological entities are introduced at a late stage of the mixing step (i.e, in the last heating zones), and more particularly when the first polymer is in a partially or totally molten state. Thus, the exposure to elevated temperature is reduced. Preferably, the residence time of the composition in the extruder is half as long as the residence time of the first polymer, or less. In another particular embodiment, the biological entities are introduced before the polymer in the extruder. Thus the contact between the composition and the polymer is increased.

According to the invention, after step (a) of preparing the masterbatch, said masterbatch may be conditioned in any suitable solid form. In this regard, in a preferred embodiment, the masterbatch is shaped into a rod through a die. The rod is then cooled, before to be chopped in the form of granulates and/or pastilles of masterbatch and optionally dried. An underwater-pelletizer may be used as well. In a further embodiment, said granulates of masterbatch may be pulverized or micronized to produce a powder of said masterbatch. It is then possible to submit the powder to an extrusion-granulation process, preferably in an extruder so that the mixture is in a partially or totally molten state, before step (b).

According to the process of the invention, the masterbatch is introduced during step (b) in a polyester-based matrix in order to produce a plastic article of the invention. The step of introducing the masterbatch in the polyester-based matrix is performed at a temperature at which both the first polymer and at least a polyester of the polyester-based matrix are in a partially or totally molten state. When the masterbatch issued of step (a) and the polyester-based matrix are in a granulated form, it is possible to submit the granulates to a step of dry-mixing before the step (b) of introduction of the masterbatch in the polyester-based matrix.

Preferably, the polyester-based matrix comprises at least one polyester chosen among copolymers of lactic acid and/or succinic acid and/or terephthalic acid or mix thereof.

Advantageously, the polyester-based matrix comprises at least one polyester chosen among polylactic acid (PLA), polyglycolic acid (PGA), polyhydroxyalkanoate (PHA), polycaprolactone (PCL), polybutylene succinate (PBS), polybutylene succinate adipate (PBSA), polybutylene adipate terephthalate (PBAT), and derivatives or blends/mixtures thereof. In a preferred embodiment, the polyester-based matrix comprises at least one polyester chosen among PLA and/or PCL and/or PBAT, more preferably PLA.

One skilled in the art is able to choose the polyester(s) of the polyester-based matrix depending on the nature of the final plastic article.

According to the invention, the polyester-based matrix may further contain at least one natural polymer and/or at least one filler and/or at least one additive.

Natural polymers may be selected from the group of lignin, polysaccharides such as cellulose or hemi-cellulose, starch, chitin, chitosan, and derivatives thereof or blends/mixtures thereof. In a particular embodiment, the natural polymers are plasticized (e.g., by a plasticizer such as water or glycerol) prior to their use for producing the masterbatch composition. Such plasticizing step modifies the chemical structure of the natural polymers allowing their use through a plastic production process.

The filler can be selected from any conventional filler used in the plastic industry. The type and exact quantity of fillers can be adapted by a person skilled in the art depending on the type of masterbatch composition and following guidance provided in the present application.

Advantageously, the plastic article comprises at least one filler selected from calcium carbonate, talc or silica.

It is the purpose of the invention to provide a process wherein a polyester-based matrix is mixed with a masterbatch that comprises a high amount of biological entities to realize a plastic article in which the biological entities is precisely added and homogeneously distributed.

According to the invention, after step (a) of mixing, and the optional conditioning of the mixture in a suitable solid form, the plastic composition produced is (b) shaped into a plastic article.

In a particular embodiment, step (b) is performed using a polyester with high melting point, i.e. with a melting point above 140° C. For instance, step (b) is performed using PLA.

Advantageously, step (b) is implemented at a temperature at which the polyester of the polyester-based matrix and the first polymer are in a partially or totally molten state. For instance, step (b) may be performed at a temperature at or above 40° C., particularly at or above 45° C., 55° C., 60° C., 70° C., 80° C., 90° C., 100° C., or even above 150° C., depending on the nature of the polymer. Typically, this temperature does not exceed 300° C. More particularly, the temperature does not exceed 250° C. Even more particularly, the temperature does not exceed 200° C. The temperature of the step (b) can be adapted by a person skilled in the art depending on the type of masterbatch and polyester-based matrix, and/or the kind of plastic articles intended. Particularly, the temperature is chosen according to the melting point, or melting temperature of the polyester of the polyester-based matrix and of the first polymer.

In a particular embodiment, step (b) is performed at the melting point of the polyester of the polyester-based matrix. The polyester is then in a partially or totally molten state. In another embodiment, step (b) is performed at a temperature between the glass transition temperature (Tg) and the melting point of said polyester. In another particular embodiment, step (b) is performed at a temperature above the melting point of said polyester.

Typically, said step (b) may be carried out by extrusion, extrusion-compounding, extrusion blow-molding, blown film extrusion, cast film extrusion, calendering and thermoforming, injection-molding, compression molding, extrusion-swelling, rotary molding, ironing, coating, stratification, expansion, pultrusion, compression-granulation, or 3D printing. Such operations are well known by the person skilled in the art, who will easily adapt the process conditions according to the kind of plastic articles intended (e.g., temperature, residence time, etc.). As an example, blown film extrusion is particularly suited for the production of plastic films. As another example, cast film extrusion is particularly suited for the production of plastic sheets, and injection-molding, thermoforming, blow-molding, rotomolding or 3D printing are particularly suited for the production of rigid plastic articles.

In a particular embodiment, step (b) is implemented with a solid masterbatch under a powder or granulated form, preferably under a granulated form.

In a particular embodiment, 0.5 to 30% by weight of masterbatch are added to the polyester-based matrix, based on the total weight of the plastic article, preferably less than 20%, more preferably less than 15%, and even more preferable less than 10%. In a particular embodiment, about 5% by weight of the masterbatch is introduced in the polyester-based matrix In another particular embodiment, 1% to 5% by weight of masterbatch is incorporated and/or mixed with 95% to 99% by weight of a polyester-based matrix in a partially or totally molten state.

In another particular embodiment, the present invention relates to a process for preparing a plastic article comprising at least PLA, comprising the steps of a) preparing a masterbatch comprising PLA-degrading biological entities and PCL by (i) heating PCL; and (ii) introducing from 5% to 50% by weight of PLA-degrading biological entities based on the total weight of the masterbatch during heating of PCL; and (b) introducing the masterbatch in a PLA-based matrix during manufacture of the plastic article Wherein step a) is performed at a temperature at which PCL is in a partially or totally molten state, preferably above 65° C., more preferably about 70° C. and wherein biological entities are introduced during step (ii) under the form of a liquid composition and step b) is performed at a temperature at which both PCL and PLA are in a partially or totally molten state, preferably above 120° C., more preferably about 155° C.

Direct Production

In another embodiment, the liquid composition of biological entities is directly introduced in the polymer(s) that composes the plastic article.

It is also an object of the invention to provide a process for preparing a plastic article as described above, comprising:

a step (a) of mixing less than 11%, particularly between 0.1% to 10% by weight of biological entities having a polyester-degrading activity, with at least said polyester, and, a step (b) of shaping said mixture of step (a) in a plastic article, wherein the biological entities are mixed during step a) under the form of a liquid composition comprising a polysaccharide carrier.

In a particular embodiment, the process further comprises a step of mixing at least one additive and/or at least a second polyester and/or a natural polymer with the polyester and biological entities, before step (b). Alternatively, such additive and/or polyester and/or natural polymer can be mixed in step (a) with the polyester and biological entities.

In a particular embodiment, the polyester used in step (a) is under a granulated form. In another embodiment, the polyester is under powder form. To this aim, the polyester can be mechanically pre-treated before step (a) of mixing, to lead to such powder forms.

Particularly, the polyester may be crushed.

Step (a) of mixing is performed at a temperature at which the polyester is in a partially or totally molten state. The step (a) of mixing may thus be performed at a temperature at or above 40° C., particularly at or above 45° C., 55° C., 60° C., 70° C., 80° C., 90° C., 100° C., or even above 150° C., depending on the nature of the polyester. Typically, this temperature does not exceed 300° C. More particularly, the temperature does not exceed 250° C. The temperature of the mixing step can be adapted by a person skilled in the art depending on the type of polyester, and/or biological entities used for the production of the plastic article. Particularly, the temperature is chosen according to the melting point, or melting temperature of the polyester. In a particular embodiment, step (a) of mixing is performed at the melting point of the polyester of the plastic article. The polyester is then in a partially or totally molten state.

In another embodiment, step (a) of mixing is performed at a temperature above the glass transition temperature of said polyester, particularly between the glass transition temperature (Tg) and the melting temperature of said polyester. In another particular embodiment, the step (a) of mixing is performed at a temperature above the melting temperature of said polyester.

In a particular embodiment, the plastic composition may be produced from step a) by a process called "compounding", usually an extrusion-granulation process, in which the polyester is melted and mixed with the biological entities. Compounding combines mixing and blending techniques during a heat process, in order to ensure uniformity, homogeneity and dispersion in the final compound. The compounding is a technique known by a person skilled in the art. Such compounding process may be carried out with an extruder, such as single-screw extruders, multi-screw extruders of either co-rotating or counter-rotating design, dispersive kneaders, reciprocating single-screw extruder (co-kneaders).

Preferably, the step (a) of mixing may be carried out with an extruder, wherein the polyester is heated and melted and mixed with the biological entities. The polyester may be introduced in the extruder in a powder or granulated form, preferably in a granulated form.

According to a particular embodiment, step (a) of mixing comprises a first step of introducing the biological entities in a first polymer that has a low melting point (below 140° C., preferably below 120° C.), such as PCL, PBSA, PBAT; and a second step wherein a polyester-based matrix comprising a second polyester that has a high melting point, such as PLA, is then added to the mixture resulting of the first step. For instance, the liquid composition is added to PCL that has been heated at about 70° C. to be in partially molten state. Then, PLA that was heated to about 150° C. to be in a partially molten state is directly added to the mixture.

In a preferred embodiment, the extruder used for the production of the plastic composition of step a) is a multi-screw extruder, preferably a twin-screw extruder, more preferably a co-rotative twin-screw extruder. In a particular embodiment, the extruder further comprises, after the screws, a static mixer. In another embodiment, the extruder is used with a die pierced with hole(s).

In a preferred embodiment, the residence time of the mixture in the extruder is comprised between 5 seconds and 3 minutes, preferably is less than 2 minutes. When the plastic composition comprises a polyester with a melting temperature below 120° C., the residence time of the mixture in the extruder is preferably less than 5 minutes.

One skilled in the art will easily adapt the characteristics of the extruder (e.g., the length and diameter of the screw(s), the screw profile, degassing zones, etc.) and the residence time to the polyester, the biological entities, and the type of plastic composition intended.

As disclosed above, the biological entities are preferably introduced in the extruder under the form of a liquid composition described above.

Particularly, such extruder may contain a principal hopper and several successive heating zones, wherein the temperature may be independently controlled and regulated and wherein additional components may be added at different time during the process. Vacuum and natural degassing zone are necessary during the extrusion to remove the volatile products like water.

The biological entities under a liquid form are introduced with a pump. In a particular embodiment, the biological entities are introduced at a late stage of the mixing step (i.e, in the last heating zones), and more particularly when the polyester is in a partially or totally molten state. Thus, the exposure to elevated temperature is reduced. Preferably, the residence time of the biological entities in the extruder is half as long as the residence time of the polyester, or less. In another particular embodiment, the liquid composition is introduced before the polyester in the extruder. Thus the contact between the composition and the polyester is increased.

According to a particular embodiment, the step (a) of mixing is carried out with two extruders, a principal extruder and a second extruder linked to the principal extruder, wherein the biological entities are mixed with a first polyester having a melting temperature below 140° C. in the second extruder, and introduced in the principal extruder in a zone wherein a polyester-based matrix is already in a partially or totally molten state, such polyester-based matrix comprising at least the polyester to be degraded by the biological entities and eventually a natural polymer selected from plasticized starch. According to a particular embodiment, the principal extruder is selected from single-screw extruder or multi-screw extruder, and the second extruder is selected from single-screw extruders, multi-screw extruders or side feeder.

According to the invention, after step (a) of mixing, the mixture may be conditioned in any suitable solid form. In this regard, in a preferred embodiment, the mixture issued from step (a) is shaped into a rod through a die. The rod is then cooled, and optionally dried before to be chopped in the form of granulates of plastic composition. In a further embodiment, said granulates of plastic composition may be pulverized or micronized to produce a powder of said plastic composition.

According to the invention, after step (a) of mixing, and the optional conditioning of the mixture in a suitable solid form, the plastic composition produced is (b) shaped into a plastic article.

Advantageously, step (b) is implemented at a temperature at which the polyester of the plastic composition is in a partially or totally molten state. For instance, step (b) may be performed at a temperature at or above 40° C., particularly at or above 45° C., 55° C., 60° C., 70° C., 80° C., 90° C., 100° C., or even above 150° C., depending on the nature of the polyester in the plastic composition. Typically, this temperature does not exceed 300° C. More particularly, the temperature does not exceed 250° C. The temperature of the step (b) can be adapted by a person skilled in the art depending on the type of the plastic composition and the polyester it comprises, and/or the kind of plastic articles intended. Particularly, the temperature is chosen according to the melting point, or melting temperature of the polyester of the plastic composition produced from step (a).

In a particular embodiment, step (b) is performed at the melting point of the polyester of the plastic composition. The polyester is then in a partially or totally molten state. In another embodiment, step (b) is performed at a temperature between the glass transition temperature (Tg) and the melting point of said polyester. In another particular embodiment, step (b) is performed at a temperature above the melting point of said polyester.

Typically, said step (b) may be carried out by extrusion, extrusion-compounding, extrusion blow-molding, blown film extrusion, cast film extrusion, calendering and thermoforming, injection-molding, compression molding, extrusion-swelling, rotary molding, ironing, coating, stratification, expansion, pultrusion, compression-granulation, or 3D printing. Such operations are well known by the person skilled in the art, who will easily adapt the process conditions according to the kind of plastic articles intended (e.g., temperature, residence time, etc.). As an example, blown film extrusionis particularly suited for the production of plastic films. As another example, cast film extrusionis particularly suited for the production of plastic sheets, and injection-molding, thermosforming, blow-molding, rotomolding or 3D printing are particularly suited for the production of rigid plastic articles.

In a preferred embodiment, step (b) is implemented with a solid plastic composition under a powder or granulated form, preferably under a granulated form.

The plastic article comprises between 0.1% and 10% by weight of the biological entities under the form of a liquid composition, based on the total weight of the plastic article.

Preferably, the liquid composition of biological entities represents between 0.1% and 5%, more preferably between 0.1% and 3% the plastic article.

According to another embodiment, the biological entities under the form of a liquid composition are directly introduced in the step (b) of shaping such plastic article.

In a particular embodiment, the present invention relates to a process for preparing a plastic composition, comprising:

a step (a) of mixing between 0.1% and 10% by weight of proteases having a PLA-degrading activity, based on the total weight of the plastic composition, with PLA and a step (b) of shaping said mixture of step (a) in a plastic article, wherein the step (a) of mixing is preferably performed at a temperature between 150 and 180° C. and/or in an extruder, preferably a twin-screw extruder, and more preferably a co-rotative twin-screw extruder.

It is a further object of the invention to provide a process for the manufacture of a plastic article containing biological entities comprising successively a step of introducing the liquid composition of the invention in a first polymer to obtain a mixture, and a step of introducing said mixture in a second polymer different from the first polymer, wherein the first polymer has melting point below 140° C. and the second polymer has a melting point above 140° C.

More generally, the plastic articles may be produced by any techniques known by a person skilled in the art.

It is also another object of the invention to provide a method for increasing the homogeneity of dispersion of biological entities in a plastic article comprising at least one polyester and said polyester-degrading biological entities, said method comprising introducing during the process of production of such plastic article, the biological entities under the form of a liquid composition.

EXAMPLES

Example 1—Use of Liquid Compositions Comprising Biological Entities, for the Manufacture of Films of the Invention Comprising PCL and PLA and Assessment of the Biodegradability of Films of the Invention 1.1—Preparation of Liquid Compositions Comprising Biological Entities Different liquid compositions have been prepared using a commercial protease, Savinase® 16L (Novozymes) sold under a liquid form (containing more than 50% by weight of polyols based on the total weight of the liquid composition and water). Such enzyme is known for its ability to degrade polylactic acid (Degradation of Polylactide by commercial proteases; Y. Oda, A. Yonetsu, T. Urakami and K. Tonomura; 2000).

Liquid composition A (LC-A) has been obtained by ultrafiltration and diafiltration of the commercial Savinase® 16L on 3.5 Kd membrane using CaCl2) 5 mM (diafiltration factor about 50). Such process enables polyols contained in the commercial Savinase® to be removed. As no carrier has been added in liquid composition A, the film produced with such composition corresponds to the negative control.

Liquid Composition B and C (LC-B and LC-C) were also obtained from the commercial liquid form of Savinase® by ultrafiltration and diafiltration on 3.5 Kd membrane using CaCl2) 5 mM (diafiltration factor about 50). Respectively, maltodextrin (Maldex—TEREOS) and arabic gum (INSTANT GUM AA—NEXIRA), were added under powder form in the filtrate at same percentage, at about 23% by weight based on the total weight of the liquid composition, in order to compare the protective effect of these two carriers. Description of the different liquid compositions is resumed in the Table 1.

TABLE 1

Description of liquid compositions which will be used to produce the articles of the invention (LC-B and LC-C) and a negative control (LC-A).

| | LC-A Without Carrier (negative control) | LC-B (Maltodextrin) | LC-C (Arabic Gum) |
|---|---|---|---|
| Carrier | 0.0% | 23.2% | 23.1% |
| Biological Entities | 31.4% | 23.3% | 23.3% |
| Aqueous solvent (water) | 67.0% | 52.3% | 52.1% |
| Others (polyols, salts) | 1.6% | 1.2% | 1.5% |
| Total | 100% | 100% | 100% |

% are given by weight, based on the total weight of the final liquid composition 1.2—Preparation of a Masterbatch Using the Composition of 1.1

Masterbatch compositions have been prepared from pellets of polycaprolactone (PCL) polymer (Cape™ 6500 from Perstorp) and compositions of the invention described in Example 1.1. Enzyme activity of said masterbatch has been further determined.

A compounding machine, or co-rotating twin-screw extruder, has been used (Leistritz ZSE 18MAXX). This compounding machine comprised nine successive heating zones Z1 to Z9, wherein the temperature may be independently controlled and regulated. An additional zone Z10 was present after zone Z9, corresponding to the head of the twin-screw (Z10) which is also a heated part. A suited screw profile was used in order to mix efficiently the liquid composition of the invention with the melt polymer. Parameters used for each extruded masterbatch are summarized in Table 2.

The molten polymer arrived in the screw Z10 comprising a die plate with one hole of 3.5 mm and was immediately immersed in a 2 m long cold water bath filled with a mix of water and crushed ice. The resulting extrudate was granulated into solid pellets<3 mm.

According to this experiment, 80% by weight of the PCL have been extruded with 20% by weight of the liquid composition.

TABLE 2

Temperature profile and process parameters of the compounding process

| Masterbatch | Composition | Temperature profile (° C.) Z1 to Z10 | Polymer Introduction Zone | Polymer Flow rate (kg/h) | Liquid composition Introduction Zone | Liquid composition Flow rate (kg/h) | Speed screw Rate (rpm) |
|---|---|---|---|---|---|---|---|
| MB1 (negative control) | PCL/LC-A (80/20) | 70-70-70-70-70-65-65-65-65-65 | Z2 | 2.6 | Z0 | 0.66 | 150 |
| MB2 | PCL/LC-B (80/20) | 70-70-70-70-70-65-65-65-65-65 | Z2 | 2.8 | Z0 | 0.7 | 175 |
| MB3 | PCL/LC-C (80/20) | 70-70-70-70-70-65-65-65-65-65 | Z2 | 2.4 | Z0 | 0.6 | 150 |

The enzyme activity in the masterbatches was determined according to the protocol described below.

50 mg of pellets were mixed with 10 mL of dichloromethane (Sigma Aldrich, CAS 75-09-2) in a 50 mL Falcon tube. Solution was mixed using a vortex (Genie2-Scientific Industrie) until the compound is totally dissolved. Then, 5 mL of 0.1 M Tris buffer pH 9.5 were added. Each tube was manually shaked in order to create an emulsion. Organic and aqueous phase were then separated by centrifugation at 10000 G during 5 min (Heraeus Multifuge X302-Thermoscientific). Aqueous phase was removed and kept separately. Another 5 mL of 0.1 M Tris buffer pH 9.5 was added to the organic phase and protocol was repeated until removing aqueous phase. Both 5 mL of aqueous phase are mixed. To remove trace of dichloromethane in the 10 mL of aqueous phase, oxygen was bubbled in the sample during 20 minutes. Protease activity of each sample was determined using colorimetric test: 20 µL of sample at the right dilution was mixed with 180 µL of a 5 mM pNA solution (N-succinyl-Ala-Ala-Ala-p-Nitroanilide, Sigma Aldrich-CAS 52299-14-6). Optical density was measured at 30° C.-420 nm using absorption spectrophotometer (Clariostar-BMG Labtech). Mass of active enzyme was thus determined using a calibration curve.

Comparing mass of active enzyme and theoretical enzyme mass in the compound enabled the percentage of residual activity in the masterbatches to be determined.

Residual activities of the masterbatches produced are resumed in the Table 3.

TABLE 3

Residual activities of masterbatches containing liquid composition

| | MB1 (negative control) PCL/LC-A | MB2 (Maltodextrin) PCL/LC-B | MB3 (Arabic gum) PCL/LC-C |
|---|---|---|---|
| Residual Activity (%) | 8% | 32% | 78% |

Masterbatches produced with the liquid compositions LC-B and LC-C demonstrate a higher residual activity compared to the masterbatch produced with a liquid composition containing no carrier (LC-A—negative control), indicating a higher protection of the enzyme during the extrusion process. Masterbatch produced with the composition comprising Arabic gum show an even better residual activity than the masterbatch produced the composition comprising maltodextrin.

1.3—Manufacture of Biodegradable Plastic Films of the Invention

The granulated masterbatch compositions of Example 1.2 were used to produce biodegradable polylactic acid-based plastic articles of the invention through an extrusion process. The biodegradability of said plastic articles was further tested.

Preparation of the PLA-Based Matrix

The PLA-based matrix was extruded using the twin screw extruder described in Example 1.2. Composition of this matrix is 42.3% by weight of PLA 4043D by NatureWorks, 51.7% by weight of PBAT PBE006 by NaturePlast and 6% by weight of $CaCO_3$ by OMYA.

All materials have been dried before extrusion. PLA and PBAT were dried about 16 hours in a desiccator at 60 and 40° C. respectively. Vacuum oven at 40° C.-40 mb for 16 h was used for calcium carbonate.

Temperature was set at 185° C. in the ten zones of the extruder. The speed screw rate was 175 rpm, and total input mass rate was about 7 kg/h. $CaCO_3$ was introduced in zone 7 to the melted polymers using a gravimetric feeder to obtain the matrix. The resulting extrudate was cooled in a cold-water bath before pelletization.

Masterbatches

Masterbatches MB1-MB2-MB3 described in Example 1.2 are used to produce the plastic films of the invention.

Film Blowing Step

Before film blowing extrusion, masterbatches and PLA-based matrix were dried in desiccator for 40 h at 50° C. Blends were prepared in order to introduce the same quantity of enzyme in all the films, based on theoretical enzyme mass in the masterbatch according to Table 4:

TABLE 4 composition of films of the invention

| Films of the invention | Matrix | MB1 (negative control) PCL/LC-A | MB2 PCL/LC-B | MB3 PCL/LC-C |
|---|---|---|---|---|
| Film A | 97% | 3% | — | — |
| Film B | 95% | — | 5% | — |
| Film C | 95% | — | — | 5% |

A LabTech compact film blowing Line type LF-250 with 20 mm 30 L/D extruder Type LBE20-30/C was used to produce films. The screw speed rate was 50 rpm. Set temperatures are detailed in Table 5.

TABLE 5

| Extruder and die temperature settings | | | | | | |
|---|---|---|---|---|---|---|
| Zone | Z1 | Z2 | Z3 | Z4 | Die #1 | Die #2 |
| T° C. | 150° C. | 150° C. | 150° C. | 150° C. | 155° C. | 155° C. |

1.4—Tests of Biodegradability

Tests of biodegradability have been performed, using plastic films produced in Example 1.3 according to the protocol set below.

100 mg of each film were weighted and introduced in a plastic bottle containing 50 mL of 0.1 M Tris buffer pH 8. The depolymerization was started by incubating each sample at 28° C., 150 rpm in a Infors HT Multitron Pro incubation shaker. Aliquots of 1 mL of buffer were sampled regularly and filtered on 0.22 µm syringe filter, samples were analyzed by High Performance Liquid Chromatography (HPLC) with an Aminex HPX-87H column to monitor the liberation of lactic acid (LA) and lactic acid dimer. Chromatography system used was an Ultimate 3000 UHPLC system (Thermo Fisher Scientific, Inc. Waltham, Mass., USA) including a pump module, an autosampler, a column oven thermostated at 50° C., and an UV detector at 220 nm. Eluent was 5 mM H2SO4. Injection was 20 µL of sample. LA was measured according to standard curves prepared from commercial LA.

Hydrolysis of plastic films was calculated based on LA and dimer of LA released. Percentage of degradation is calculated regarding the percentage of PLA in the films.

Results of the depolymerization of the films of the invention, after 2 days, are shown in Table 6.

TABLE 6

| Comparison of the depolymerization of the films of the invention (B and C) and a negative control | |
|---|---|
| | Depolymerization rate after 2 days |
| Film A (negative control) Comprising MB1 (PCL/LC-A) | 0.002% |
| Film B Comprising MB2 (PCL/LC-B - MaltoDextrin) | 9.6% |
| Film C Comprising MB3 (PCL/LC-C- Arabic Gum) | 11.6% |

Films of the invention (MB2/LC-B and MB3/LC-C) show a higher depolymerization rate, due to a higher residual activity as compared to the control film produced with a liquid composition deprived of carrier (MB1/LC-A—negative control). These results confirm that the use of the liquid composition comprising a carrier leads to a higher protection of the enzyme during the extrusion process. Film produced with the composition of comprising Arabic gum shows an even better degradability than the film produced with the composition comprising maltodextrin.

Example 2—Preparation of a Liquid Composition, Use of Such Composition for the Production of Films of the Invention and Assessment of the Mechanical and Degradation Properties of Such Films 2.1—Preparation of Compositions Comprising Biological Entities A liquid composition LC has been prepared from a commercial protease, Savinase® 16L (Novozymes). LC has been obtained by ultrafiltration and diafiltration of the commercial Savinase® 16L using CaCl2 5 mM (diafiltration factor about 100) on 3.5 Kd membrane to obtain a concentrated liquid composition and to remove polyols present in the commercial solution. About 23% of Arabic gum (INSTANT GUM AA—NEXIRA), based on the total weight of the liquid composition, was then added as a carrier in the liquid composition which is designated as LC.

A solid composition was also prepared according to the same protocol using a commercial protease, Savinase® 16L and the protocol set above. The liquid composition obtained was concentrated, and was then dried by freeze drying to obtain a solid composition called SC. Comparisons of the different compositions are summarized in the Table 7.

TABLE 7

| Liquid and solid compositions | | |
|---|---|---|
| Enzyme composition | Liquid composition (LC) | Solid composition (SC) |
| Aqueous solvent (water) | 51.3% | 0.5% |
| Carrier (Arabic gum) | 23.3% | 15.7% |
| Biological entities | 23.0% | 33% |
| Others including polyols (glycerol, propylene glycol) and other additives | 2.4% | 50.8% |

% are given by weight, based on the total weight of the final liquid composition.

2.2—Preparation Masterbatches

Masterbatches have been prepared with pellets of polycaprolactone polymer (PCL—Capa™ 6500 from Perstorp) and the liquid or solid compositions of 2.1, using the same compounding machine as in Example 1.2.

More particularly, a masterbatch comprising PCL and the liquid enzyme composition LC from Example 2.1 was produced. The PCL and LC were introduced separately in the extruder at the feeding zone which is a non-heated zone. For feeding, a gravimetric feeder was used for the polymer and a peristaltic pump for the liquid composition. The obtained masterbatch was called MB-L.

In parallel, a masterbatch comprising PCL and the solid enzyme composition SC from Example 2.1 was produced. SC was introduced in Zone 7 using a gravimetric feeder suited for dosing solid in powder from. The obtained masterbatch was designated MB-S.

Parameters used for masterbatche extrusion are detailed in table 8 and table 9. A suited screw profile was used in order to mix efficiently the corresponding compositions with the polymer.

TABLE 8

| | Extruder temperature settings | | | | | | | | | |
|---|---|---|---|---|---|---|---|---|---|---|
| Zone | Z1 | Z2 | Z3 | Z4 | Z5 | Z6 | Z7 | Z8 | Z9 | Z10 (die) |
| MB-L Temperature | 70° C. | 70° C. | 70° C. | 70° C. | 70° C. | 65° C. | 65° C. | 65° C. | 65° C. | 65° C. |
| MB-S Temperature | 70° C. | 70° C. | 70° C. | 70° C. | 70° C. | 70° C. | 70° C. | 70° C. | 70° C. | 70° C. |

TABLE 9

Extrusion parameters used for masterbatches

| | Composition | Screw speed rate (rpm) | Total input flow rate (kg/h) |
|---|---|---|---|
| MB-L | 72% Capa™ 6500 + 28% LC | 150 | 3 |
| MB-S | 70% Capa™ 6500 + 30% SC | 150 | 3.5 |

The molten polymer arrived in the screw Z10 comprising a die plate with one hole of 3.5 mm and was immediately immersed in a 2 m long cold-water bath filled with a mix of water and crushed ice. The resulting extrudate was granulated into solid pellets<3 mm.

2.3—Production of Films of the Invention

A—Preparation of the PLA-Based Matrix

Three different matrixes were used for the production of the films: two commercial compounds Ecovio® F2332 and Ecovio® F2223 from BASF, and a Home compounded matrix called Matrix 1.

Matrix 1 was manufactured using a twin-screw extruder CLEXTRAL EV25HT comprising twelve zones Z1 to Z12, wherein the temperature is independently controlled and regulated. The compound is composed of 33% of pre-plasticized PLA containing 10% by weight of tributyl acetyl citrate (CITROFOL® BII from Jungbunzlauer), 32% of PBAT Ecoflex C1200 supplied by BASF, 30% of thermoplastic starch where the starch is standard maize starch 171111 supplied by Roquette and 5% of calcium carbonate from OMYA. The starch is introduced in zone 1 and the polymers in zone 6, wherein the zones are heated according to Table 10. This compound is designated as Matrix 1.

TABLE 10

| | Extruder temperature settings | | | | | | | | | | | |
|---|---|---|---|---|---|---|---|---|---|---|---|---|
| Zone | Z1 | Z2 | Z3 | Z4 | Z5 | Z6 | Z7 | Z8 | Z9 | Z10 | Z11 | Z12 |
| Matrix 1 Temperature | 50° C. | 70° C. | 70° C. | 80° C. | 90° C. | 150° C. | 150° C. | 150° C. | 150° C. | 150° C. | 150° C. | 150° C. |

B—Production of the Films of the Invention with Liquid Composition (MB-L)

For film blowing, a LabTech compact film blowing Line type LF-250 with 20 mm 30 L/D extruder Type LBE20-30/C was used. The screw speed rate used was 60 rpm. Blow ratio of film was about 5 for an objective of 17 μm.

Before film blowing, the MB-L (example 2.2) and the different PLA-based matrix were dried in a desiccator for 40 h at 50° C. Then MB-L was mixed to the PLA-based matrix with a weight ratio PLA to masterbatch of 93/7.

Films obtained with PLA-based matrix Ecovio® F2332 and Ecovio® F2223 were designated as Film 1 and Film 2 respectively, and Table 11 shows the parameters used for extrusion.

TABLE 11

| | Extruder and die temperature settings | | | | | | |
|---|---|---|---|---|---|---|---|
| Film | Zone | Z1 | Z2 | Z3 | Z4 | Die #1 | Die #2 |
| Film 1 (ecovio® F2332) | T° C. | 145 | 150 | 150 | 150 | 155 | 155 |
| Film 2 (ecovio® F2223) | T° C. | 150 | 151 | 151 | 153 | 155 | 157 |

The film produced with Matrix 1 was designated as Film 3 and Table 12 shows the parameters used for extrusion.

TABLE 12

| | Extruder and die temperature settings | | | | | | |
|---|---|---|---|---|---|---|---|
| Sample | Zone | Z1 | Z2 | Z3 | Z4 | Die #1 | Die #2 |
| Film 3 (Matrix 1) | T° C. | 145 | 147 | 148 | 148 | 148 | 150 |

C— Production of the Control Films with Solid Composition (MB-S)

PLA-based matrix Ecovio® F2332 and Ecovio® F2223 and the Matrix 1 were used to produce films with the masterbatch comprising the solid composition of biological entities and were respectively designated as Film 4, Film 5 and Film 6.

Before film blowing, the MB-S and PLA-based matrix were dried in a desiccator for 40 h at 50° C. An additional masterbatch comprising only PCL and Arabic gum 70/30 w/w was added to the mixture MB-S/PLA-based matrix in order to obtain the same biological entities concentration in all the films of the invention.

Finally, the films were made by use of 93% by weight of a PLA-based matrix and 7% by weight of a mixture of both masterbatches (MB-S and additional masterbatch).

Films 1 and 4, Film 2 and 5, and Film 3 and 6 respectively have same compositions. Then MB-S was dry-mixed to the PLA-based matrix and introduced in the film blowing extruder.

The same process as for films 1, 2 and 3 was used to produce the films, except the temperature profile as shown in table 13:

TABLE 13

| | Extruder and die temperature settings | | | | | | |
|---|---|---|---|---|---|---|---|
| Film | Zone | Z1 | Z2 | Z3 | Z4 | Die #1 | Die #2 |
| Films 4, 5 and 6 | T° C. | 135 | 147 | 147 | 150 | 152 | 150 |

2.4—Evaluation of Mechanical Properties and Biodegradability of the Plastic Films of the Invention The films of the invention in example 2.3 were analysed according for the following parameters:

A. Haze

Haze is determined using a spectrometer UV-Visible Perkin Elmer 650S equipped with a 150 mm integrating sphere according to NF EN 2155-9 (August 1989). The values are determined on a 50×30 mm² sample. On each film, the measurements are repeated 3 times on 3 different parts of the film.

B. Surface Roughness (Dynamic Friction Coefficient)

The dynamic friction coefficient ($\mu_D$) is measured according to standard NF EN ISO-8295 (December 2004) which fits for plastic film or plastic sheet with a thickness below 0.5 mm. It is determined using a Lloyd Instruments LS5 testing machine equipped with a 20N sensor capacity. The apparatus comprises a horizontal test table on which the first sample is placed, a mass generating the press force (1.96 N) and to which the second sample is attached, and a traction mechanism to produce a relative movement between the mass and the test table. The mass is pulled and moved on the test table (test speed=500 mm/min).

The measure is precise about 0.01%. The sample dimensions are the followings: 80 mm×200 mm.

The dynamic friction force FD is the average force on the 6 first centimeters of relative movement.

C. Mechanical tensile properties and thickness

Tensile mechanical properties (elongation at break, tensile stress at break, Young's modulus) were determined using a Zwick testing machine equipped with 50N sensor capacity according to ASTM D882-12 standard (at 23° C. and 55% RH). Two film directions: machine direction and transverse direction were analyzed with the following parameters:

Rate of grip separation for Young's modulus=10 mm/min
Rate of grip separation for other properties=50 mm/min
Initial grip separation: 100 mm,
Sample dimensions: 150 mm×15 mm.
Average thickness: 17 μm Thickness used for tensile analysis was determined based on the film weights, dimensions and densities. This choice was made to overcome the overestimations of the thickness due to the presence of aggregates of particles in the surface of the film especially when solid compositions are used.

Nevertheless, measurement of the thickness can be done using a Mitutoyo thickness gauge to demonstrate the surface roughness observed for films containing aggregates.

D. Depolymerization Test

The protocol was same as the one used in Example 1.4.

E. Results and Comparison

The results obtained for the film of the invention produced with the liquid composition was compared to the results obtained for the film produced with the solid composition: Film 1 versus Film 4; Film 2 versus Film 5 and Film 3 versus Film 6.

Mechanical Properties

Table 14 shows the Haze results measured on Film 1, 2, 4 and 5. The Haze values of the films of the invention 1 and 2 are respectively lower than the ones of 4 and 5. Haze is caused by impurities contained in the plastic article (such as accumulation of tiny particles in the article or very small defects on the surface). The lower the Haze value, the higher the clarity of the article is. The films of the invention produced from a liquid composition thus show a lower Haze, thus a better dispersion of the biological entities than the control films.

TABLE 14

| Haze results determined for films produced from liquid or solid enzyme compositions | | | | | |
|---|---|---|---|---|---|
| Characteristic Composition | Unit | Film 1 ecovio ® F2332 + MB-L | Film 4 ecovio ® F2332 + MB-S | Film 2 ecovio ® F2223 + MB-L | Film 5 ecovio ® F2223 + MB-S |
| Haze | % | 86.6 | 92.4 | 85.5 | 88.1 |
| | Base 100 | 93.3 | 100 | 97 | 100 |

Table 15 and 16 show the dynamic friction coefficient, tensile properties and thickness measured by Mitutoyo thickness gauge of the films produced in 2.3. "s" corresponds to the standard deviation in the same unit as the characteristic measured.

TABLE 15

| Dynamic friction coefficient, tensile properties and thickness of films | | | | | | | | |
|---|---|---|---|---|---|---|---|---|
| Characteristic | Test direction | Unit | Film 1 | Film 4 | Film 2 | Film 5 | Film 3 | Film 6 |
| Composition | | | ecovio ® F2332 + MB-L | ecovio ® F2332 + MB-S | ecovio ® F2223 + MB-L | ecovio ® F2223 + MB-S | Matrix 1 + MB-L | Matrix 1 + MB-S |
| Thickness (Mitutoyo) | | μm | 20 | 55 | 21 | 43 | 25 | 60 |
| Dynamic friction coefficient | MD | N s | 0.352 0.09 | 0.376 0.009 | 0.266 0.007 | 0.357 0.005 | 0.241 0.01 | 0.287 0.007 |
| Young modulus | MD | MPa s | 220 8 | 285 5 | 992 59 | 708 62 | 1020 91 | 645 66 |
| | TD | MPa | 145 | 139 | 297 | 218 | 618 | 394 |

TABLE 15-continued

Dynamic friction coefficient, tensile properties and thickness of films

| Characteristic | Test direction | Unit | Film 1 | Film 4 | Film 2 | Film 5 | Film 3 | Film 6 |
|---|---|---|---|---|---|---|---|---|
| | | s | 2 | 6 | 5 | 10 | 82 | 14 |
| Strain at | MD | % | 250 | 210 | 220 | 120 | 140 | 33 |
| break | | s | 21 | 11 | 3 | 8 | 11 | 8 |
| | TD | % | 480 | 310 | 200 | 65 | 46 | 12 |
| | | s | 7 | 6 | 22 | 9 | 10 | 2 |
| Ultimate | MD | MPa | 23.9 | 24.1 | 33.5 | 16.1 | 18.1 | 9.5 |
| tensile | | s | 0.9 | 0.8 | 1.2 | 1.3 | 1 | 0.6 |
| strength | TD | MPa | 21.4 | 15.4 | 14.7 | 9.1 | 13 | 6 |
| | | s | 1 | 0.8 | 1.1 | 0.3 | 1.5 | 0.7 |

In Table 16, films produced from MB-S are used as a reference and considered as 100% of the defined parameter.

TABLE 16

Dynamic friction coefficient and tensile properties of films on base 100

| Characteristic | Test direction | Unit | Film 1 | Film 4 | Film 2 | Film 5 | Film 3 | Film 6 |
|---|---|---|---|---|---|---|---|---|
| Composition | | | ecovio ® F2332 + MB-L | ecovio ® F2332 + MB-S | ecovio ® F2223 + MB-L | ecovio ® F2223 + MB-S | Matrix 1 + MB-L | Matrix 1 + MB-S |
| Dynamic friction coefficient | MD | N | 93.6 | 100 | 74.5 | 100 | 84 | 100 |
| Young modulus | MD | MPa | 77 | 100 | 140 | 100 | 158 | 100 |
| | TD | MPa | 104 | 100 | 136 | 100 | 156 | 100 |
| Strain at break | MD | % | 119 | 100 | 183 | 100 | 424 | 100 |
| | TD | % | 154 | 100 | 307 | 100 | 383 | 100 |
| Ultimate tensile strength | MD | MPa | 99 | 100 | 208 | 100 | 191 | 100 |
| | TD | MPa | 139 | 100 | 161 | 100 | 218 | 100 |

Friction coefficient is the ratio between the sliding force and the holding force of two surfaces in contact. This coefficient characterizes the difficulty of two materials to slide on each other. This difficulty can be increased in case of surface roughness. Dynamic friction coefficient values of the films of the invention 1, 2 and 3 are lower than the ones of films 4, 5 and 6 respectively indicating less surface roughness. Using a liquid composition during the production process then allows to reduce the dynamic friction coefficient and by this way to reduce the surface roughness in comparison of using a solid composition of biological entities.

This characteristic was also visible to the naked eye: films 4, 5, 6 show irregularity on the surface due to particles aggregates.

Measurement of the thickness using a Mitutoyo thickness gauge also demonstrates this surface roughness observed for films produced from solid composition of biological entities leading to aggregates in the film.

Young modulus, strain at break and ultimate tensile strength measured for films of the invention are significantly higher than control films. The liquid composition has smaller particle size that leads to a fine and homogeneous dispersion of particles in the film and as consequent to an improvement of mechanical properties.

Depolymerization Test

Depolymerization test showed that films of the invention have a significantly higher percentage of depolymerization rate compared to those obtained with solid enzyme composition, as shown in Table 17 (films from Ecovio® F2332), Table 18 (films from Ecovio® F2223) and Table 19 (films from Matrix 1). Films produced from MB-S are used as a reference and considered as 100.

TABLE 17

Case of ecovio ® F2332 - Level of depolymerisation after 16 days

| | | Enzyme composition | Level of depolymerization |
|---|---|---|---|
| Film 4 | ecovio ® F2332 + MB-S | solid | 100 |
| Film 1 | ecovio ® F2332 + MB-L | liquid | 775 |

TABLE 18

Case of ecovio ® F2223- Level of depolymerisation after 16 days

| | | Enzyme composition | Level of depolymerization |
|---|---|---|---|
| Film 5 | ecovio ® F2223 + MB-S | solid | 100 |
| Film 2 | ecovio ® F2223 + MB-L | liquid | 3000 |

TABLE 19

Case of Matrix1- Level of depolymerisation after 2 days

| | | Enzyme composition | Level of depolymerization |
|---|---|---|---|
| Film 6 | Matrix 1 + MB-S | solid | 100 |
| Film 3 | Matrix 1 + MB-L | liquid | 776 |

2.5—Production of Rigid Plastic Article

An injection molding machine was used for the production of rigid plastic articles: KM 50t/380 CX ClassiX type with MC6 computer controller system.

The rigid plastic articles were produced by the incorporation of the masterbatch MB-L of Example 2.2 in two types of polyester-based matrix. The matrixes are chosen from two polylactic acid polymer grades whose characteristics are shown in Table 20.

TABLE 20

Characteristics of the polyester-based matrix used for the production of rigid plastic articles

| Polyester-based matrix | Specific gravity (g/cm³) | MFI (g/10 min) | Melting temperature (° C.) |
|---|---|---|---|
| PLI 003 NaturePlast | 1.25 | 35 (190° C./ 2.16 kg) | 155-170 |
| PLA 4043D Ingeo Natureworks | 1.24 | 6 (210° C./ 2.16 kg) | 145-160 |

Before dry-mixing, polyester-based matrix and masterbatch were dried in desiccator at 50° C. for 40 h. 10% of MB-L was then added to the polyester-based matrix. Articles with 100% polyester-based matrix were also produced for comparison.

A 60 mm×60 mm with 1 mm thick pieces were manufactured by injection molding process.

Parameters were set depending on the grade of polyester-based matrix acid used.

The parameters set for injection molding are summarized in Table 21.

TABLE 21

Extrusion parameters used for production of rigid articles by injection

| | Composition | Set temperatures in barrel zones, from feed zone to the front zone (° C.) | Injection pressure (bar) | Hold pressure (bar) | Molding cycle (s) | Mold temperature (° C.) |
|---|---|---|---|---|---|---|
| PA1 (control versus PA2) | PLI 003 NaturePlast | 35/160/160/165/170 | 1040 | 1000 | 41.6 | 30 |
| PA2 | PLI 003 NaturePlast + 10% MB-L | 35/160/160/165/170 | 1035 | 900 | 43 | 30 |
| PA3 (control versus PA4) | PLA 4043D Ingeo Natureworks | 35/155/155/160/160 | 2300 | 800 | 32.6 | 30 |
| PA4 | PLA 4043D Ingeo Natureworks + 10% MB-L | 35/155/155/160/160 | 1900 | 800 | 32.6 | 30 |

Total composition residence time in the barrel was measured and is about 12 min for PA1 and PA2 and 13 min for PA3 and PA4.

The rigid articles produced were submitted to a depolymerization test, according to the protocol described in Example 1.4. The results are shown in Table 22, PA1 and PA3 are used as reference and considered as 100. They demonstrate that the use of the composition of the invention enables to produce biodegradable rigid plastic articles.

TABLE 22

Depolymerization test for the injection molding plastic articles

| Sample | Level of depolymerization at 10 days |
|---|---|
| PA1 (control) | 100 |
| PA2 | 1500 |

TABLE 23

Depolymerization test for the injection molding plastic articles

| Sample | Level of depolymerization at 10 days |
|---|---|
| PA3 (control) | 100 |
| PA4 | 4267 |

Example 3—Preparation of a Masterbatch Using a Liquid Composition, Use of Such Masterbatch for the Production of a PLA-Based Rigid Article of the Invention and Assessment of the Tensile, Impact and Biodegradability Properties of Such Article 3.1—Preparation of a Masterbatch Using a Liquid Composition Masterbatches were prepared using pellets of polycaprolactone (PCL) polymer (Capa™ 6500 from Perstorp) and liquid or solid enzymatic composition described in Table 24. Liquid composition LC-1 and solid composition SC-1 were prepared with same manner as detailed in example 2.1.

TABLE 24

Enzymatic compositions used for producing the masterbatches

| Enzyme composition | Liquid composition LC-1 | Solid composition SC-1 |
|---|---|---|
| Aqueous solvent (water) | 53.8% | 3.2% |
| Dry matter including | 46.2% including | 96.8% including |
| Carrier (Arabic gum) | −22.4% | −77.4% |
| Biological entities | −19.8% | −19.4% |
| Others including polyols and salts | −4% | |

% are given by weight, based on the total weight of the final liquid composition The masterbatch MB-LC1 comprising PCL and the liquid composition LC-1 was prepared using a twin-screw extruder Clextral Evolum 25 HT comprising twelve zones Z1 to Z12, wherein the temperature is independently controlled and regulated. The parameters used for the process are the following: temperature profile 65° C.–65° C.–65° C.–65° C.–65° C.–65° C.–65° C.–65° C.–65° C.–65° C.–65° C.–50° C., extruder screws speed of 450 rpm, and a total flow rate of 40 kg/h. The PCL is introduced in Zone 1 at 32 kg/h and the liquid composition LC-1 in Zone 5 at 8 kg/h using a volumetric pump. 20% of the liquid enzymatic composition was introduced to the PCL based on the total weight of the extruded masterbatch.

In parallel, a masterbatch MB-SC1 comprising PCL and the solid composition SC-1 was prepared on a co-rotating twin-screw extruder (Leistritz ZSE 18MAXX) with the following parameters: temperature profile of 70° C.–70° C.–70° C.–70° C.–70° C.–65° C.–65° C.–65° C.–65° C.–65° C., screws speed of 150 rpm, and a total flow rate of 2 kg/h. 22% of the solid enzymatic composition was introduced to the PCL based on the total weight of the masterbatch using a gravimetric feeder in Zone 7. The cooling and granulation system of both masterbatches were the same as detailed in Example 1.2.

Both masterbatches MB-LC1 and MB-SC1 thus comprise the same enzymatic concentration.

3.2—Production of Rigid Plastic of the Invention by Injection Molding

Plastic dumbbells having thickness of 4 mm and a total length of 170 mm were produced using an injection molding machine (KM 50t/380 CX ClassiX).

Dumbbells were produced from an injection PLA grade NatureWorks® Ingeo™ 3251D and the masterbatch MB-LC1 described in 3.1. Control dumbbells were produced from same PLA grade and masterbatch MB-SC1 described in 3.1. 100% PLA dumbbells were also produced for standardized mechanical characterization.

Before manufacturing the rigid articles, PLA and MB-LC1 were dried using a desiccator for 40 h at 50° C. and MB-SC1 was dried in a vacuum oven at 50° C. for 48 h. The rigid plastic articles were made by use of 95% by weight of the PLA-based matrix and 5% by weight of a masterbatch.

Injection molding parameters for each article are detailed in Table 25:

TABLE 25

Injection molding parameters for dumbbells production

| | Composition | Set temperatures in barrel zones, from feed zone to the front zone (° C.) | Injection pressure (bar) | Hold pressure (bar) | Molding cycle (s) | Mold temperature (° C.) |
|---|---|---|---|---|---|---|
| RA-LC1 | 95% PLA + 5% MB-LC1 | 40/145/150/150/160/160 | 1000 | 850 | 70 | 30 |
| RA-SC1 | 95% PLA + 5% MB-SC1 | 40/145/150/150/160/160 | 1005 | 900 | 70 | 30 |

3.3—Tensile and Impact Characterization of Plastic Articles

Tensile and impact properties of the rigid plastic article of the invention and of the control plastic article made from a solid composition were characterized.

Tensile Test

Tensile tests were carried using a Zwick Roell testing machine equipped with 20 kN force sensor. The tests were carried out according to ISO 527-1 standard and the results of the test are shown in Table 26.

TABLE 26

Tensile properties of the rigid plastic article of the invention (RA-LC1) and control (RA-SC1)

| Sample | Elastic Modulus (GPa) | Maximum stress $\sigma m$ (MPa) | Strain at maximum stress $\varepsilon m$ (%) | Stress at break $\sigma b$ (MPa) | Strain at break $\varepsilon b$ (%) |
|---|---|---|---|---|---|
| RA-LC1 | 2.2 | 55 | 3 | 55 | 3 |
| RA-SC1 | 2.2 | 56 | 3 | 57 | 3 |

Rigid article produced from a masterbatch from a liquid composition does not show significant difference in measured mechanical characteristics showing that the use of a liquid composition has no severe impact on the elastic Modulus, maximum stress, strain at maximum stress, stress at break and strain at break of the rigid article of the invention.

Charpy Impact Test

Tests were carried according to the NF EN ISO 179-1 Standard using a Zwick pendulum impact tester. Test bars were cut from the injected specimens using a heated cutting plier. Bars dimensions are 4 mm*10 mm*80 mm. The results of the test are shown in Table 27.

TABLE 27

Impact properties of the rigid plastic article of the invention (RA-LC1) and control (RA-SC1)

| Sample | Impact strength (KJ/m$^2$) |
|---|---|
| RA-LC1 | 21.81 |
| RA-SC1 | 15.19 |

Rigid article of the invention produced from a liquid composition of biological entities shows a better impact resistance than those produced from a solid biological entities composition.

This is certainly due to the fine distribution of the biological entities in the plastic article.

3.4—Depolymerization Test

Tests of biodegradability have been performed, on injected rigid article RA-LC1 produced from the liquid composition. Firstly, the rigid article was coarsely ground, immersed in liquid nitrogen and then ground using Ultra-Centrifugal Mill ZM 200 RETSCH equipped with a 500 µm grid. 100 mg of this powder were weighted, introduced and confined in the dialysis tube. The tube was placed in 50 mL of 0.1 M Tris buffer pH 9.5. The depolymerization was started by incubating each sample at 45° C., 150 rpm in a Infors HT Multitron Pro incubation shaker. Aliquots of 1 mL of buffer were sampled regularly and filtered on 0.22 µm syringe filter, samples were analyzed by High Performance Liquid Chromatography (HPLC) with an Aminex HPX-87H column to monitor the liberation of lactic acid (LA) and lactic acid dimer. Chromatography system used was an Ultimate 3000 UHPLC system (Thermo Fisher Scientific, Inc. Waltham, Mass., USA) including a pump module, an autosampler, a column oven thermostated at 50° C., and an UV detector at 220 nm.

Eluent was 5 mM H2SO4. Injection was 20 µL of sample. LA was measured according to 20 standard curves prepared from commercial LA.

The level of depolymerization of the rigid article reached about 10% after 48 h showing the biological entities retain a polyester degrading activity in the final plastic article.

Example 4—Preparation of a Masterbatch Using a Liquid Composition, Use of Such Masterbatch for the Production of Rigid Sheets of the Invention and Assessment of the Tensile, Impact and Degradation Properties of Such Sheets

4.1—Preparation of a Masterbatch Using a Liquid Composition

Masterbatch composition has been prepared from pellets of polycaprolactone (PCL) polymer (Capa™ 6500 from Perstorp) and the liquid enzymatic composition LC-1 described in example 3.1. The masterbatch was manufactured using a co-rotating twin-screw extruder CLEXTRAL EV25HT comprising twelve zones Z1 to Z12, wherein the temperature is independently controlled and regulated.

The PCL is introduced in zone 1 at 16 kg/h and the liquid composition in zone 5 at 4 kg/h using a peristaltic pump, wherein the zones are heated according to Table 27. 20% of the liquid composition LC was introduced to the PCL based on the total weight of the masterbatch. This masterbatch is designated as MB-LC2.

TABLE 27

Extruder temperature settings for the production of the masterbatch

| Zone | | Z1 | Z2 | Z3 | Z4 | Z5 | Z6 | Z7 | Z8 | Z9 | Z10 | Z11 | Z12 |
|---|---|---|---|---|---|---|---|---|---|---|---|---|---|
| MB-LC2 | Temperature | 90 | 65 | 65 | 65 | 65 | 65 | 65 | 65 | 65 | 65 | 65 | 65 |

The enzyme activity in the masterbatch was determined according to the protocol described in Example 1.2. Comparing mass of active enzyme and theoretical enzyme mass in the masterbatch enabled the percentage of residual activity in the masterbatches to be determined.

4.2—Manufacture of Biodegradable Plastic Sheets of the Invention

A thermoforming PLA grade Total Corbion Luminy® LX175 was used for manufacturing 450 µm thick plastic sheets to be submitted to further standardized impact and tensile characterization and test of biodegradability.

For plastic sheets manufacturing, an extruder FAIREX comprising four zones Z1 to Z4, wherein the temperature is independently controlled and regulated with a diameter of 45, a flat die of 220 mm equipped with an adjustable lip at 1.5 mm of nominal opening and a three cylinders calender was used.

Before extrusion and calendaring, the MB-LC2 and the PLA were dried and mixed together. The MB-LC2 was dried 20 hours at 40° C. in vacuum oven and the PLA was dried 4 hours at 40° C. in dryers.

Sheets obtained from 0% (negative control), 5% or 10% of MB-LC2 added on PLA were respectively designated S0, S5 and S10. The extrusion and calendaring parameters are detailed in Table 28.

TABLE 28

Extruder and calender settings for sheets production

| | S0 | S5 | S10 |
|---|---|---|---|
| Composition | 100% PLA | 95% PLA + 5% MB-LC | 90% PLA + 10% MB-LC |

TABLE 28-continued

Extruder and calender settings for sheets production

|  | S0 | S5 | S10 |
|---|---|---|---|
| Set temperatures in extruder zones, from Z1 to Z4 (° C.) | 165-165-180-180 | 160-170-175-175 | 160-165-170-170 |
| Screw speed rate (rpm) | 50 | 50 | 49 |
| Pressure (bar) | 150.5 | 154 | 150.5 |
| Die temperature (° C.) | 175 | 170 | 165 |
| Lip opening (mm) | 0.6 | 0.6 | 0.6 |

TABLE 28-continued

Extruder and calender settings for sheets production

|  | S0 | S5 | S10 |
|---|---|---|---|
| Cylinder temperature (° C.) | 40 | 40 | 40 |
| Flow rate (kg/h) | 24.5 | 23 | 23 |

4.3—Evaluation of Biodegradability of the Plastic Sheets

In order to evaluate the biodegradability of the plastic sheets a depolymerization test was performed following the protocol already described in Example 3.4.

After 8 days, the powder of the sheets S0, S5 and S10 show respectively a depolymerization rate of the PLA of 0.08%, 0.77% and 13.0% showing that the biological entities retain a polyester degrading activity in the final plastic article of the invention (S5 and S10).

4.4—Dart-Test Characterization of Plastic Sheets

Impact tests were carried out according to NF EN ISO 7765-1, using the steps method. According to this standard, the sample where cut directly on the plastic sheet. The tests were performed using a Labthink BMC-B1 Dart-test machine and the results are presented in Table 29.

TABLE 29

Impact properties of plastic sheets

|  | m50 (kg) | E50 (J) |
|---|---|---|
| S0 | 0.158 | 1.0 |
| S5 | 0.293 | 1.9 |
| S10 | 0.353 | 2.3 |

The results of the impact test show that the sheets of the invention produced from liquid composition (S5 and S10) show an improvement of impact resistance compared to the control S0 made of 100% PLA.

4.5—Tensile Characterization of Plastic Sheets

Tensile tests were carried using a Zwick Roell testing machine equipped with 20 kN force sensor. The tests were carried out according to NF EN ISO 527-1 standard. The tensile properties measured are presented in Table 30.

TABLE 30

Tensile properties of plastic sheets

|  | Test direction - thickness | Elastic modulus (GPa) | Maximum stress σm (MPa) | Strain at maximum stress εm (%) | Stress at break σb (MPa) | Strain at break εb (%) |
|---|---|---|---|---|---|---|
| S0 | MD - 452 μm | 1.91 | 68 | 4 | 60 | 6 |
|  | TD - 452 μm | 1.89 | 66 | 3.6 | 66 | 3.6 |
| S5 | MD - 462 μm | 1.79 | 61 | 3.9 | 56 | 4.5 |
|  | TD - 464 μm | 1.70 | 58 | 3.7 | 56 | 3.8 |
| S10 | MD - 485 μm | 1.94 | 63 | 4 | 60 | 4.3 |
|  | TD - 474 μm | 1.65 | 45 | 3 | 18.3 | 17 |

Comparing to a pure PLA sheet (S0), sheets produced from a masterbatch itself produced from a liquid composition and PCL, show an improvement of flexibility with the increase of incorporation of such masterbatch in PLA based sheets, while maintaining enough stiffness required for the intended application.

Example 5—Preparation of a Masterbatch Using a Liquid Composition, Use of Such Masterbatch for the Production of Films of the Invention Comprising PCL and PLA

5.1—Preparation of Liquid Compositions

Different liquid compositions have been prepared using a commercial protease, Savinase® 16L (Novozymes) sold under a liquid form.

Liquid composition D, E, F and G were obtained according to the method described in Example 1.1: ultrafiltration and diafiltration of the commercial Savinase® 16L on 3.5 Kd membrane and wherein arabic gum is added as carrier. The commercial Savinase® 16L sold under a liquid form, corresponds to the liquid composition H and is used as a negative control. Such composition comprises more than 50% by weight of polyols, as a carrier, based on the total weight of the liquid composition and water.

Description of the different liquid compositions is resumed in the Table 31.

TABLE 31

Description of liquid compositions (LC-D, LC-E, LC-F and LC-G) and a negative control (LC-H).

|  | LC-D | LC-E | LC-F | LC-G | LC-H Commercial Savinase 16L (negative control |
|---|---|---|---|---|---|
| Dry matter (%) including | 25.4% including | 46.9% including | 66.0% including | 48.7% including | 75% including |
| Biological entities having PLA Depolymerase Activity | 10.9% | 21.9% | 31.7% | 6.9% | 4.5% |
| Carrier Others including polyols and salts | 12.3% 2.2% | 23.1% 1.9% | 31.8% 2.5% | 40.3% 1.5% | 0% 70.5% |
| Aqueous solvent (water) | 74.6% | 53.1% | 34% | 51.3% | 25% |
| Total | 100% | 100% | 100% | 100% | 100% |

% are given by weight, based on the total weight of the final liquid composition

5.2—Preparation of Masterbatches Using Compositions of 5.1

Masterbatch compositions have been prepared from pellets of polycaprolactone (PCL) polymer (Capa™ 6500 from Perstorp) and compositions described in Example 3.1, using the same compounding machine as in Example 1.2.

According to this experiment, 80% by weight of the PCL have been extruded with 20% by weight of the liquid composition. Parameters used for each extruded masterbatch are summarized in Table 32.

TABLE 32

Temperature profile and process parameters of the compounding process

| Masterbatch | Composition | Temperature profile (° C.) Z1 to Z10 | Polymer Introduction Zone | Polymer Flow rate (kg/h) | Liquid composition Introduction Zone | Liquid composition Flow rate (kg/h) | Speed screw Rate (rpm) |
|---|---|---|---|---|---|---|---|
| MB4 | PCL/LC-D (80/20) | 70-70-70-70-70-65-65-65-65-65 | Z2 | 1.99 | Z0 | 0.51 | 150 |
| MB5 | PCL/LC-E (80/20) | 70-70-70-70-70-65-65-65-65-65 | Z2 | 2.64 | Z0 | 0.66 | 150 |
| MB6 | PCL/LC-F (80/20) | 70-70-70-70-70-65-65-65-65-65 | Z2 | 1.28 | Z0 | 0.32 | 150 |
| MB7 | PCL/LC-G (80/20) | 70-70-70-70-70-65-65-65-65-65 | Z2 | 2.32 | Z0 | 0.58 | 150 |
| MB8 (negative control) | PCL/LC-H (80/20) | 70-70-70-70-70-65-65-65-65-65 | Z2 | 2.16 | Z0 | 0.54 | 150 |

Enzyme activity of said masterbatch has been further determined using the protocol described in Example 1.2. Comparing mass of active enzyme and theoretical enzyme mass in the masterbatch enabled the percentage of residual activity in the masterbatches to be determined. Residual activities of the masterbatches produced are resumed in the Table 33.

TABLE 33

Residual activities of masterbatches containing liquid composition of the invention

|  | MB4 PCL/LC-D | MB5 PCL/LC-E | MB6 PCL/LC-F | MB7 PCL/LC-G | MB8 (negative control) PCL/LC-H |
|---|---|---|---|---|---|
| Residual Activity (%) | 22.8% +/− 0.2% | 85.1% +/− 9.5% | 67.3% +/− 6.3% | 71.7% +/− 9.0% | 0% |

All masterbatches produced with liquid compositions (LC-D to LC-G) demonstrate a high residual activity. On the opposite, MB8 containing Savinase 16L and corresponding to the negative control, does not show any residual activity. This result confirms the interest in extrusion process of liquid compositions comprising a specific carrier compared to commercial formulation already described.

MB5 and MB7, which have similar water content (or similar dry matter) but different content of biological entities, show equivalent residual activity. This result tends to indicate that protection of the biological entities is equivalent, whatever the percentage of engaged biological entities.

Additionally, MB4, produced from the composition containing the highest quantity of water as compared to compositions used to produce MB5, MB6 or MB7, show the lowest residual activity. This result tends to indicate that protection of the biological entities is increased when the quantity of the aqueous solvent is below 70%, preferably below 60% and/or when the quantity of dry matter is above 30%, preferably above 40%, independently from the quantity of biological entities introduced in the liquid composition.

5.3—Manufacture of Biodegradable Plastic Films of the Invention

The granulated masterbatch compositions MB4, MB5 and MB6 of Example 5.2 were used to produce biodegradable polylactic acid-based plastic articles of the invention through an extrusion process. The biodegradability of said plastic articles was further tested.

Preparation of the PLA-Based Matrix

The PLA-based matrix was extruded using the twin screw extruder described in Example 1.2. Composition of this matrix is 42.3% by weight of PLA 4043D by NatureWorks, 51.7% by weight of PBAT PBE006 by NaturePlast and 6% by weight of $CaCO_3$ by OMYA. All materials have been dried before extrusion. PLA and PBAT were dried about 5 hours in a desiccator at 60 and 40° C. respectively. Vacuum oven at 40° C.-40 mb for 16 h was used for calcium carbonate.

Temperature was set at 185° C. in the ten zones of the extruder. The speed screw rate was 175 rpm, and total input mass rate was about 5 kg/h. $CaCO_3$ was introduced in zone 7 to the melted polymers using a gravimetric feeder to obtain the PLA-based matrix. The resulting extrudate was cooled in a cold-water bath before pelletizing.

Masterbatches

Masterbatches MB4-MB5-MB6 described in Example 5.2 are used to produce the plastic films of the invention.

Film Blowing Step

Before film blowing extrusion, masterbatches and PLA-based matrix were dried in vacuum oven at 50° C.-40 mb for 15 h. Blends were prepared in order to introduce the same quantity of enzyme in all the films, based on theoretical enzyme mass in the masterbatch and according to Table 34. For Film E and F, it was necessary to add PCL 6500 (also dried following the same conditions) in order to obtain identical composition in all the films.

TABLE 34 composition of manufactured films

| Film reference | PLA-based Matrix | MB4 PCL/ LC-D | MB5 PCL/ LC-E | MB6 PCL/ LC-F | PCL 6500 |
|---|---|---|---|---|---|
| Film D (P1340/Fi-01) | 90% | 10% | — | — | — |
| Film E (P1341/Fi-01) | 90% | — | 4.2% | — | 5.8% |
| Film F (P1342/Fi-01) | 90% | — | — | 4.8% | 5.2% |

Blowing was realized using the same machine and parameters described in example 1.3.

5.4—Tests of Biodegradability

Tests of biodegradability have been performed on plastic films produced in Example 5.3, according to the protocol described in example 1.4.

Hydrolysis of plastic films was calculated based on LA and dimer of LA released.

Percentage of degradation is calculated regarding the percentage of PLA in the films.

Results of the depolymerization of the films, after 4 days, are shown in Table 35.

TABLE 35

Comparison of the depolymerization of the films of the invention produced from masterbatches themselves produced from the liquid compositions LC-D, LC-E, and LC-F.

| | Depolymerization after 4 days |
|---|---|
| Film D - Comprising MB4 (PCL/LC-D) | 15.3% |
| Film E - Comprising MB5 (PCL/LC-E) | 23.7% |
| Film F - Comprising MB6 (PCL/LC-F) | 44.7% |

All films of the invention show a high depolymerization rate, indicating presence of active enzyme. The more the liquid formulation contain dry matter, the more degradation yield reached is high in the film of the invention. This result confirms that a higher dry matter in the composition of the invention results in a higher protection of the biological entities during both extrusion processes (masterbatch production and plastic article production).

Example 6—Preparation of a Masterbatch Using a Liquid Composition, Use of Such Masterbatch for the Production of Films of the Invention Comprising PLA

6.1—Preparation of Masterbatches Using the Composition of the Invention and PLA and Assessment of Residual Activity of Such Masterbatches The liquid composition LC-1 from example 3.1 and two grades of polylactic acid (PLA) were used for manufacturing masterbatches: an amorphous grade Luminy LX930U from Total Corbion (melting temperature below 140° C.) and a semi-crystalline grade Ingeo™ Biopolymer 4043D from NatureWorks (melting temperature above 140° C.).

Polylactic acid based masterbatches designated as MB-PLA1, MB-PLA2 and MB-PLA3 were prepared on a co-rotating twin-screw extruder (Leistritz ZSE 18MAXX) with screws speed of 150 rpm and a total flow rate of 2 kg/h. Extrusion temperatures are detailed in Table 36 below. The PLA was introduced in the non-heated feeding zone (Z0), and LC-1 was introduced in Z6 using a Brabender pump. The cooling and granulation system of both masterbatches were the same as detailed in Example 1.2. Composition of the masterbatches are also showed in Table 36.

TABLE 36

Temperature profile and process parameters of the compounding process

| | Composition | Zone | Z1 | Z2 | Z3 | Z4 | Z5 | Z6 | Z7 | Z8 | Z9 | Z10 (die) |
|---|---|---|---|---|---|---|---|---|---|---|---|---|
| MB PLA 1 | 80% PLA LX930U + 20% LC-1 | Temperature | 135° C. | 135° C. | 135° C. | 135° C. | 135° C. | 120° C. | 120° C. | 120° C. | 120° C. | 120° C. |
| MB-PLA 2 | 90% PLA LX930U + 10% LC-1 | Temperature | 135° C. | 135° C. | 135° C. | 135° C. | 135° C. | 120° C. | 120° C. | 120° C. | 120° C. | 120° C. |
| MB-PLA 3 | 90% PLA 4043D + 10% LC-1 | Temperature | 145° C. | 145° C. | 145° C. | 145° C. | 145° C. | 130° C. | 130° C. | 130° C. | 130° C. | 130° C. |

Tests of biodegradability have been performed, using masterbatches produced above according to the protocol set in Example 3.4 and level of depolymerization after 24 h are shown in table 37.

TABLE 37

Level of depolymerization of masterbatches

| | Level of depolymerization after 24 h |
|---|---|
| MB-PLA1 | 92.70% |
| MB-PLA2 | 84.60% |
| MB-PLA3 | 10.50% |

Masterbatches based on PLA LX930U with lower melting point (MB-PLA1 and MB-PLA2), showed higher depolymerization levels than that of MB-PLA3 based on PLA4043D for which higher extrusion temperatures have been used (even at equivalent quantity of biological entities). The activity of the enzyme in the liquid composition LC-1 is thus significantly better maintained in lower process temperature using a PLA with a melting temperature below 140° C.

6.2—Production of the Films and Evaluation of Biodegradability

MB-PLA1 or MB-PLA2, and PLA based matrix from the Example 1.3 (42.3% by weight of PLA 4043D by NatureWorks, 51.7% by weight of PBAT PBE006 by NaturePlast and 6% by weight of $CaCO_3$ by OMYA) were used for the production of films. Before film blowing extrusion, masterbatches and PLA-based matrix were dried in vacuum oven at 60° C. for 5 h. Compositions of blends prepared are shown in Table 38.

TABLE 38

Composition of manufactured films

| Films | PLA based matrix | MB-PLA1 | MB-PLA2 |
|---|---|---|---|
| Film 7 | 90% | 10 | — |
| Film 8 | 90% | — | 10 |
| Film 9 | 80% | — | 20 |

The film blowing line used and set temperatures are the same as the Example 1.3. The screw speed rate set was 60 rpm. Cooling air amplitude and drawing speed were adjusted to obtain a bubble width of 200 mm a film thickness between 15 and 20 µm.

Tests of biodegradability have been performed on the films produced above according to the protocol set in Example 1.4 and level of depolymerization after 26 days are shown in table 39.

TABLE 39

Level of depolymerization of films

| Film | Percentage of depolymerization after 26 days |
|---|---|
| Film 7 | 13.4% |
| Film 8 | 5.5% |
| Film 9 | 8.6% |

The films produced from a masterbatch comprising PLA with a melting temperature below 140° C. and the composition of the invention all showed degradation in aqueous media. Film 7 and Film 9 are supposed to contain the same quantity of biological entities, but the Film 7 based on the most concentrated masterbatch (MB-PLA1 produced from 20% of LC-1) shows a higher level of degradation than Film 9 based on MB-PLA2 produced from 10% of LC-1. However, the results show that the liquid composition of the invention is also suitable to be introduced in a partially or totally molten polymer having a melting point above 140° C. and that the biological entities still preserve a polymer degrading activity in the masterbatch.

Example 7—Manufacture of Rigid Plastic Article of the Invention Comprising PLA and PCL by 3D Printing

7.1—Preparation of Masterbatch Using a Liquid Composition and Assessment of the Residual Activity of Such Masterbatch The liquid composition LC-1 from example 3.1 has been used for masterbatch preparation.

The same extruder and the same parameters as Example 1.2 were used to prepare a masterbatch composed of 90% of PCL (Capa™ 6500 from Perstorp) and 10% of liquid composition LC-1 designated as MB9, a screw speed of 150 rpm and a total flow rate of 2 kg/h were set.

The enzyme activity in the masterbatch was determined according to the protocol described in Example 1.2. The residual activity of MB9 is 87%.

7.2 Filament Manufacturing and 3D Printing of Rigid Plastic Article Comprising PLA and PCL A PLA based filament was manufactured using Ingeo™ Biopolymer 4043D from NatureWorks. Before filament extrusion, masterbatch MB9 and PLA were dried for 15 h at 50° C. in a vacuum oven. Masterbatch was dry-blended with PLA in a ratio 30%/70% in weight and then extruded in a single screw extruder (Scamex-Rheoscam, Ø20-11 L/D) at 100° C.–170° C.–190° C. set in the three zones of the extruder and 180° C. in the die. A screw speed rate of 47 rpm was used. The extrudate was cooled with pressurized air, the final diameter of the filament was about 1.75 mm.

A cartesian type printer was used. This printer, Neocore model, has a basalt plateau of 30×30 cm that can heat up to 200° C. and a single-nozzle E3D equipped with a system of BondTech filament that can heat up to 400° C. The 3D printing tests were conducted using 5A tensile specimen geometry according to ISO 537-2. 3D printing parameters are detailed in Table 40.

TABLE 40

| 3D printing parameters | |
| --- | --- |
| Nozzle diameter | 0.4 mm |
| Layer thickness | 0.2 mm |
| Nozzle temperature | 170° C. |
| Plateau temperature | 40° C. |
| Printing speed | 65 to 70 mm/s |
| Specimen dimension | 75 × 12.5 × 2 mm (volume = 1.203 cm3) |

7.3 Depolymerization Test

Depolymerization tests were carried on 100 mg of micronized 5A tensile specimen (1 mm grid) using the same protocol as in Example 3.4. The depolymerization of the specimen reach 11% in buffer pH 9.5 at 45° C. after 8 days (dialysis system). Depolymerization results confirm that biological entities retain polymer degrading activity in a 3D printed plastic article produced from the composition of the invention, even after a second heating at high temperature during the 3D printing.

The invention claimed is:

1. A process for preparing a plastic article comprising at least one polyester and at least one enzyme having a polyester-degrading activity homogeneously dispersed in the plastic article, said process comprising:
   a step (a) of mixing between 0.01% and 10% by weight of at least one enzyme having a polyester-degrading activity with a least said one polyester, and
   a step (b) of shaping said mixture of step (a) in a plastic article,
   wherein the at least one enzyme is mixed during step (a) under the form of a masterbatch comprising the at least one enzyme having a polyester-degrading activity, a polysaccharide carrier selected from natural gums and a carrier polymer having a melting temperature below 140° C. and/or a glass transition temperature below 70° C.

2. The process according to claim 1, wherein the step (a) of mixing is performed at a temperature at which the polyester is in a partially or totally molten state and/or in an extruder.

3. The process of claim 1, wherein the polyester has a melting temperature above 140° C.

4. The process of claim 1, wherein the polyester is selected from (co)polymers of lactic acid and/or succinic acid and/or terephthalic acid.

5. The process of claim 1, wherein the natural gums are selected from arabic gum, guar gum, tragacanth gum, karaya gum and mixtures thereof.

6. The process of claim 1, wherein the carrier polymer having a melting temperature below 140° C. and/or a glass transition temperature below 70° C. is a polyester selected from polycaprolactone (PCL), poly butylene succinate adipate (PBSA), polybutylene adipate terephthalate (PBAT), polydioxanone (PDS), polyhydroxyalkanoate (PHA), polylactic acid (PLA) and mixtures thereof.

7. A masterbatch comprising at least one enzyme having a polyester-degrading activity, a polysaccharide carrier selected from natural gums and a carrier polymer having a melting temperature below 140° C. and/or a glass transition temperature below 70° C.

8. The masterbatch of claim 7, wherein the carrier polymer having a melting temperature below 140° C. and/or a glass transition temperature below 70° C. is a selected among a polyester, starch, EVA and mixtures thereof.

9. The masterbatch of claim 8, wherein the carrier polymer having a melting temperature below 140° C. and/or a glass transition temperature below 70° C. is selected among polycaprolactone (PCL), polybutylene succinate adipate (PBSA), polybutylene adipate terephthalate (PBAT), polydioxanone (PDS), polyhydroxyalkanoate (PHA), polylactic acid (PLA), and mixtures thereof.

10. The masterbatch of claim 8, wherein the carrier polymer having a melting temperature below 140° C. and/or a glass transition temperature below 70° C. is selected among polycaprolactone (PCL), EVA, PBAT, PLA and mixtures thereof.

11. The masterbatch of claim 7, comprising from 50% to 95% by weight of carrier polymer having a melting temperature below 140° C. and/or a glass transition temperature below 70° C. based on the total weight of the masterbatch.

12. The masterbatch of claim 11, comprising from 70% to 90% by weight of carrier polymer having a melting temperature below 140° C. and/or a glass transition temperature below 70° C.

13. The masterbatch of claim 7, wherein the at least one enzyme comprises an enzyme having a polyester-degrading activity.

14. The masterbatch of claim 7, comprising from 5% to 50% by weight of the at least one enzyme based on the total weight of the masterbatch.

15. The masterbatch of claim 14, comprising from 10% to 30% of the at least one enzyme.

16. The masterbatch of claim 7, wherein the natural gums are is selected from arabic gum, guar gum, tragacanth gum, karaya gum and mixtures thereof.

17. The masterbatch of claim 7, wherein the natural gum is arabic gum.

18. The masterbatch of claim 7, comprising from 1% to 30% of polysaccharide carrier.

19. The masterbatch of claim 18, wherein it comprises from 1% to 15% of polysaccharide carrier.

20. A process for preparing a masterbatch comprising at least one enzyme having a polyester-degrading activity, a polysaccharide carrier selected from natural gums and a carrier polymer having a melting temperature below 140° C. and/or a glass transition temperature below 70° C., said process comprising mixing a liquid composition comprising the enzymes and the polysaccharide carrier with the carrier polymer at a temperature at which the carrier polymer is in a partially or totally molten state.

21. The method of claim 20, wherein the liquid composition and the carrier polymer are mixed in an extruder.

22. The method of claim 20, wherein the liquid composition comprises, based on the total weight of the composition:
from 0.01% to 35% by weight of the at least one enzyme;
from 15% to 95% by weight of an aqueous solvent; and
from 3% to 80% by weight of a polysaccharide carrier.

23. The method of claim 20, wherein the polymer having a melting temperature below 140° C. and/or a glass transition temperature below 70° C. is a polyester selected from polycaprolactone (PCL), polybutylene succinate adipate (PBSA), polybutylene adipate terephthalate (PBAT), polydioxanone (PDS), polyhdroxyalkanoate (PHA), polylactic acid (PLA) and mixtures thereof.

24. The method of claim 20, wherein the at least one enzyme is a protease.

25. The method of claim 20, wherein the natural gums are selected from arabic gum, guar gum, tragacanth gum, karaya gum and mixtures thereof.

26. The process of claim 1, wherein the at least one enzyme is supplied in a liquid form.

27. The process of claim 1, wherein the masterbatch is prepared by mixing a liquid composition comprising the enzymes and the polysaccharide carrier with the carrier polymer at a temperature at which the carrier polymer is in a partially or totally molten state.

* * * * *